United States Patent
Yokoyama et al.

(10) Patent No.: US 6,833,258 B2
(45) Date of Patent: Dec. 21, 2004

(54) PROCESS FOR PRODUCING TRANSGLUTAMINASE

(75) Inventors: Keiichi Yokoyama, Kawasaki (JP); Kunio Ono, Kawasaki (JP); Daisuke Ejima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/892,864

(22) Filed: Jun. 28, 2001

(65) Prior Publication Data
US 2002/0090675 A1 Jul. 11, 2002

Related U.S. Application Data

(63) Continuation of application No. PCT/JP99/07250, filed on Dec. 24, 1999.

(30) Foreign Application Priority Data

Dec. 28, 1998 (JP) ............................................ 10-373131

(51) Int. Cl.[7] .......................... C12N 9/10; A61K 38/45; A23J 3/20
(52) U.S. Cl. .......................... 435/193; 424/94.5; 426/61
(58) Field of Search ........................ 435/193; 424/94.5; 426/61

(56) References Cited

U.S. PATENT DOCUMENTS 5,827,712 A  10/1998  Yokoyama et al. .......... 435/193
6,013,498 A   1/2000  Yokoyama et al. .......... 475/193

FOREIGN PATENT DOCUMENTS

EP    0 331 464    9/1989
EP    0 336 324   10/1989

OTHER PUBLICATIONS

M. Kawai et al., "High–Level Expression of the Chemically Synthesized Gene for Microbial Transglutaminase from Streptoverticillium in *Escherichia coli*", *Biosci. Biotech. Biochem*, 1997, vol. 61, No. 5, pp. 830–835.

D. Ejima, et al., "High Yield Refoding and Purification Process for Recombinant Human Interlukin–6 Expressed in *Escherichia coli*", *Biotechnology and Bioengineering*, Feb. 5, 1999, vol. 62, No. 3, pp. 301–310.

*Primary Examiner*—Charles L. Patterson, Jr.
(74) *Attorney, Agent, or Firm*—Oblon, Spivak, McClelland, Maier & Neustadt, P.C.

(57) ABSTRACT

The present invention relates to a high-yield process for producing high-activity, high-purity transglutaminase by refolding denatured microorganism-derived transglutaminase by reacting denatured transglutaminase in an aqueous medium under acidic conditions and reconstituting a higher-order enzymatically active state in an aqueous medium at a neutral pH.

39 Claims, 12 Drawing Sheets

FIG. 6

```
pUCTRPMTG(+)02  :  ···TTTAAATGGATTCTGACGAT···
                          M  D  S  D  D pUCTRPMTG(+)D2  :  ···TTTAAATG---TCTGACGAT···
                          M     S  D  D

Natural-type MTG :            D  S  D  D
```

- is a deleted base

FIG. 7

```
MTG in pUCTRPMTG(+)D2  :  SDDRV····

For reference
  Natural-type MTG     :  DSDDRV····
  MTG in pUCTRPMTG(+)02 : MDSDDRV····
```

1 2 3 4

SEQUENCE LISTING

<160> NUMBER OF SEQ ID NOS: 58

<210> SEQ ID NO 1
<211> LENGTH: 1519
<212> TYPE: DNA
<213> ORGANISM: Artificial Sequence
<220> FEATURE:
<223> OTHER INFORMATION: Synthetic DNA
<221> NAME/KEY: CDS
<222> LOCATION: (87)..(1082)
<223> OTHER INFORMATION:

<400> SEQUENCE: 1

```
ttcccctgtt gacaattaat catcgaacta gttaactagt acgcaagttc acgtaaaaag      60
ggtatcgatt agtaaggagg tttaaa atg gat tct gac gat cgt gtt act cca      113
                              Met Asp Ser Asp Asp Arg Val Thr Pro
                              1               5 cca gct gaa cca ctg gat cgt atg cca gat cca tat cgt cca tct tat      161
Pro Ala Glu Pro Leu Asp Arg Met Pro Asp Pro Tyr Arg Pro Ser Tyr
 10              15                  20                  25 ggt cgt gct gaa act gtt gtt aat aat tat att cgt aaa tgg caa caa      209
Gly Arg Ala Glu Thr Val Val Asn Asn Tyr Ile Arg Lys Trp Gln Gln
             30                  35                  40 gtt tat tct cat cgt gat ggt cgt aaa caa caa atg act gaa gaa caa      257
Val Tyr Ser His Arg Asp Gly Arg Lys Gln Gln Met Thr Glu Glu Gln
         45                  50                  55 cgt gaa tgg ctg tct tat ggt tgc gtt ggt gtt act tgg gtt aac tct      305
Arg Glu Trp Leu Ser Tyr Gly Cys Val Gly Val Thr Trp Val Asn Ser
     60                  65                  70 ggt cag tat ccg act aac cgt ctg gca ttc gct tcc ttc gat gaa gat      353
Gly Gln Tyr Pro Thr Asn Arg Leu Ala Phe Ala Ser Phe Asp Glu Asp
 75                  80                  85 cgt ttc aag aac gaa ctg aag aac ggt cgt ccg cgt tct ggt gaa act      401
Arg Phe Lys Asn Glu Leu Lys Asn Gly Arg Pro Arg Ser Gly Glu Thr
 90                  95                 100                 105 cgt gct gaa ttc gaa ggt cgt gtt gct aag gaa tcc ttc gat gaa gag      449
Arg Ala Glu Phe Glu Gly Arg Val Ala Lys Glu Ser Phe Asp Glu Glu
             110                 115                 120 aaa ggc ttc cag cgt gct cgt gaa gtt gct tct gtt atg aac cgt gct      497
Lys Gly Phe Gln Arg Ala Arg Glu Val Ala Ser Val Met Asn Arg Ala
         125                 130                 135 cta gag aac gct cat gat gaa tct gct tac ctg gat aac ctg aag aag      545
Leu Glu Asn Ala His Asp Glu Ser Ala Tyr Leu Asp Asn Leu Lys Lys
     140                 145                 150 gaa ctg gct aac ggt aac gat gct ctg cgt aac gaa gat gct cgt tct      593
Glu Leu Ala Asn Gly Asn Asp Ala Leu Arg Asn Glu Asp Ala Arg Ser
 155                 160                 165 ccg ttc tac tct gct ctg cgt aac act ccg tcc ttc aaa gaa cgt aac      641
Pro Phe Tyr Ser Ala Leu Arg Asn Thr Pro Ser Phe Lys Glu Arg Asn
170                 175                 180                 185 ggt ggt aac cat gat ccg tct cgt atg aaa gct gtt atc tac tct aaa      689
Gly Gly Asn His Asp Pro Ser Arg Met Lys Ala Val Ile Tyr Ser Lys
             190                 195                 200 cat ttc tgg tct ggt cag gat aga tct tct tct gct gat aaa cgt aaa      737
His Phe Trp Ser Gly Gln Asp Arg Ser Ser Ser Ala Asp Lys Arg Lys
         205                 210                 215 tac ggt gat ccg gat gca ttc cgt ccg gct ccg ggt act ggt ctg gta      785
Tyr Gly Asp Pro Asp Ala Phe Arg Pro Ala Pro Gly Thr Gly Leu Val
     220                 225                 230
```

```
gac atg tct cgt gat cgt aac atc ccg cgt tct ccg act tct ccg ggt      833
Asp Met Ser Arg Asp Arg Asn Ile Pro Arg Ser Pro Thr Ser Pro Gly
    235                 240                 245 gaa ggc ttc gtt aac ttc gat tac ggt tgg ttc ggt gct cag act gaa      881
Glu Gly Phe Val Asn Phe Asp Tyr Gly Trp Phe Gly Ala Gln Thr Glu
250                 255                 260                 265 gct gat gct gat aag act gta tgg acc cat ggt aac cat tac cat gct      929
Ala Asp Ala Asp Lys Thr Val Trp Thr His Gly Asn His Tyr His Ala
                270                 275                 280 ccg aac ggt tct ctg ggt gct atg cat gta tac gaa tct aaa ttc cgt      977
Pro Asn Gly Ser Leu Gly Ala Met His Val Tyr Glu Ser Lys Phe Arg
            285                 290                 295 aac tgg tct gaa ggt tac tct gac ttc gat cgt ggt gct tac gtt atc     1025
Asn Trp Ser Glu Gly Tyr Ser Asp Phe Asp Arg Gly Ala Tyr Val Ile
        300                 305                 310 acc ttc att ccg aaa tct tgg aac act gct ccg gac aaa gtt aaa cag     1073
Thr Phe Ile Pro Lys Ser Trp Asn Thr Ala Pro Asp Lys Val Lys Gln
    315                 320                 325 ggt tgg ccg taatgaaagc ttggatctct aattactgga cttcacacag             1122
Gly Trp Pro
330 actaaaatag acatatctta tattatgtga ttttgtgaca tttcctagat gtgaggtgga   1182 ggtgatgtat aaggtagatg atgatcctct acgccggacg catcgtggcc ggcatcaccg   1242 gcgccacagg tgcggttgct ggcgcctata tcgccgacat caccgatggg aagatcggg    1302 ctcgccactt cgggctcatg agcgcttgtt tcggcgtggg tatggtggca ggccccgtgg   1362 ccgggggact gttgggcgcc atctccttgc atgcaccatt ccttgcggcg gcggtgctca   1422 acggcctcaa cctactactg ggctgcttcc taatgcagga gtcgcataag ggagagcgtc   1482 gagagcccgc ctaatgagcg gcttttttt tcagctg                             1519

<210> SEQ ID NO 2
<211> LENGTH: 332
<212> TYPE: PRT
<213> ORGANISM: Artificial Sequence
<220> FEATURE:
<223> OTHER INFORMATION: Synthetic Peptide

<400> SEQUENCE: 2

Met Asp Ser Asp Asp Arg Val Thr Pro Pro Ala Glu Pro Leu Asp Arg
1               5                   10                  15

Met Pro Asp Pro Tyr Arg Pro Ser Tyr Gly Arg Ala Glu Thr Val Val
            20                  25                  30

Asn Asn Tyr Ile Arg Lys Trp Gln Gln Val Tyr Ser His Arg Asp Gly
        35                  40                  45

Arg Lys Gln Gln Met Thr Glu Glu Gln Arg Glu Trp Leu Ser Tyr Gly
    50                  55                  60

Cys Val Gly Val Thr Trp Val Asn Ser Gly Gln Tyr Pro Thr Asn Arg
65                  70                  75                  80

Leu Ala Phe Ala Ser Phe Asp Glu Asp Arg Phe Lys Asn Glu Leu Lys
                85                  90                  95

Asn Gly Arg Pro Arg Ser Gly Glu Thr Arg Ala Glu Phe Glu Gly Arg
            100                 105                 110

Val Ala Lys Glu Ser Phe Asp Glu Glu Lys Gly Phe Gln Arg Ala Arg
        115                 120                 125

Glu Val Ala Ser Val Met Asn Arg Ala Leu Glu Asn Ala His Asp Glu
    130                 135                 140
```

```
Ser Ala Tyr Leu Asp Asn Leu Lys Lys Glu Leu Ala Asn Gly Asn Asp
145                 150                 155                 160

Ala Leu Arg Asn Glu Asp Ala Arg Ser Pro Phe Tyr Ser Ala Leu Arg
            165                 170                 175

Asn Thr Pro Ser Phe Lys Glu Arg Asn Gly Asn His Asp Pro Ser
        180                 185                 190

Arg Met Lys Ala Val Ile Tyr Ser Lys His Phe Trp Ser Gly Gln Asp
        195                 200                 205

Arg Ser Ser Ser Ala Asp Lys Arg Lys Tyr Gly Asp Pro Asp Ala Phe
        210                 215                 220

Arg Pro Ala Pro Gly Thr Gly Leu Val Asp Met Ser Arg Asp Arg Asn
225                 230                 235                 240

Ile Pro Arg Ser Pro Thr Ser Pro Gly Glu Gly Phe Val Asn Phe Asp
        245                 250                 255

Tyr Gly Trp Phe Gly Ala Gln Thr Glu Ala Asp Ala Asp Lys Thr Val
            260                 265                 270

Trp Thr His Gly Asn His Tyr His Ala Pro Asn Gly Ser Leu Gly Ala
        275                 280                 285

Met His Val Tyr Glu Ser Lys Phe Arg Asn Trp Ser Glu Gly Tyr Ser
        290                 295                 300

Asp Phe Asp Arg Gly Ala Tyr Val Ile Thr Phe Ile Pro Lys Ser Trp
305                 310                 315                 320

Asn Thr Ala Pro Asp Lys Val Lys Gln Gly Trp Pro
            325                 330

<210> SEQ ID NO 3
<211> LENGTH: 39
<212> TYPE: DNA
<213> ORGANISM: Artificial Sequence
<220> FEATURE:
<223> OTHER INFORMATION: Synthetic DNA

<400> SEQUENCE: 3
aattcatcga ttagtaagga ggtttaaaat ggattctga                      39

<210> SEQ ID NO 4
<211> LENGTH: 41
<212> TYPE: DNA
<213> ORGANISM: Artificial Sequence
<220> FEATURE:
<223> OTHER INFORMATION: Synthetic DNA

<400> SEQUENCE: 4
cgatcgtcag aatccatttt aaacctcctt actaatcgat g                   41

<210> SEQ ID NO 5
<211> LENGTH: 41
<212> TYPE: DNA
<213> ORGANISM: Artificial Sequence
<220> FEATURE:
<223> OTHER INFORMATION: Synthetic DNA

<400> SEQUENCE: 5
cgatcgtgtt actccaccag ctgaaccact ggatcgtatg c                   41

<210> SEQ ID NO 6
<211> LENGTH: 41
<212> TYPE: DNA
<213> ORGANISM: Artificial Sequence
<220> FEATURE:
<223> OTHER INFORMATION: Synthetic DNA
```

```
<400> SEQUENCE: 6
gatctggcat acgatccagt ggttcagctg gtggagtaac a          41

<210> SEQ ID NO 7
<211> LENGTH: 41
<212> TYPE: DNA
<213> ORGANISM: Artificial Sequence
<220> FEATURE:
<223> OTHER INFORMATION: Synthetic DNA

<400> SEQUENCE: 7
cagatccata tcgtccatct tatggtcgtg ctgaaactgt t          41

<210> SEQ ID NO 8
<211> LENGTH: 41
<212> TYPE: DNA
<213> ORGANISM: Artificial Sequence
<220> FEATURE:
<223> OTHER INFORMATION: Synthetic DNA

<400> SEQUENCE: 8
attaacaaca gtttcagcac gaccataaga tggacgatat g          41

<210> SEQ ID NO 9
<211> LENGTH: 41
<212> TYPE: DNA
<213> ORGANISM: Artificial Sequence
<220> FEATURE:
<223> OTHER INFORMATION: Synthetic DNA

<400> SEQUENCE: 9
gttaataatt atattcgtaa atggcaacaa gtttattctc a          41

<210> SEQ ID NO 10
<211> LENGTH: 41
<212> TYPE: DNA
<213> ORGANISM: Artificial Sequence
<220> FEATURE:
<223> OTHER INFORMATION: Synthetic DNA

<400> SEQUENCE: 10
tcacgatgag aataaacttg ttgccattta cgaatataat t          41

<210> SEQ ID NO 11
<211> LENGTH: 41
<212> TYPE: DNA
<213> ORGANISM: Artificial Sequence
<220> FEATURE:
<223> OTHER INFORMATION: Synthetic DNA

<400> SEQUENCE: 11
tcgtgatggt cgtaaacaac aaatgactga agaacaacgt g          41

<210> SEQ ID NO 12
<211> LENGTH: 41
<212> TYPE: DNA
<213> ORGANISM: Artificial Sequence
<220> FEATURE:
<223> OTHER INFORMATION: Synthetic DNA

<400> SEQUENCE: 12
gccattcacg ttgttcttca gtcatttgtt gtttacgacc a          41

<210> SEQ ID NO 13
```

```
<211> LENGTH: 42
<212> TYPE: DNA
<213> ORGANISM: Artificial Sequence
<220> FEATURE:
<223> OTHER INFORMATION: Synthetic DNA

<400> SEQUENCE: 13
aatggctgtc ttatggttgc gttggtgtta cttgggttaa ca                42

<210> SEQ ID NO 14
<211> LENGTH: 40
<212> TYPE: DNA
<213> ORGANISM: Artificial Sequence
<220> FEATURE:
<223> OTHER INFORMATION: Synthetic DNA

<400> SEQUENCE: 14
agcttgttaa cccaagtaac accaacgcaa ccataagaca                  40

<210> SEQ ID NO 15
<211> LENGTH: 38
<212> TYPE: DNA
<213> ORGANISM: Artificial Sequence
<220> FEATURE:
<223> OTHER INFORMATION: Synthetic DNA

<400> SEQUENCE: 15
aattcgttaa ctctggtcag tatccgacta accgtctg                    38

<210> SEQ ID NO 16
<211> LENGTH: 41
<212> TYPE: DNA
<213> ORGANISM: Artificial Sequence
<220> FEATURE:
<223> OTHER INFORMATION: Synthetic DNA

<400> SEQUENCE: 16
cgaatgccag acggttagtc ggatactgac cagagttaac g                41

<210> SEQ ID NO 17
<211> LENGTH: 49
<212> TYPE: DNA
<213> ORGANISM: Artificial Sequence
<220> FEATURE:
<223> OTHER INFORMATION: Synthetic DNA

<400> SEQUENCE: 17
gcattcgctt ccttcgatga agatcgtttc aagaacgaac tgaagaacg        49

<210> SEQ ID NO 18
<211> LENGTH: 49
<212> TYPE: DNA
<213> ORGANISM: Artificial Sequence
<220> FEATURE:
<223> OTHER INFORMATION: Synthetic DNA

<400> SEQUENCE: 18
ggacgaccgt tcttcagttc gttcttgaaa cgatcttcat cgaaggaag        49

<210> SEQ ID NO 19
<211> LENGTH: 35
<212> TYPE: DNA
<213> ORGANISM: Artificial Sequence
<220> FEATURE:
<223> OTHER INFORMATION: Synthetic DNA

<400> SEQUENCE: 19
```
gtcgtccgcg ttctggtgaa actcgtgctg aattc          35

<210> SEQ ID NO 20
<211> LENGTH: 35
<212> TYPE: DNA
<213> ORGANISM: Artificial Sequence
<220> FEATURE:
<223> OTHER INFORMATION: Synthetic DNA

<400> SEQUENCE: 20
gaccttcgaa ttcagcacga gtttcaccag aacgc          35

<210> SEQ ID NO 21
<211> LENGTH: 48
<212> TYPE: DNA
<213> ORGANISM: Artificial Sequence
<220> FEATURE:
<223> OTHER INFORMATION: Synthetic DNA

<400> SEQUENCE: 21
gaaggtcgtg ttgctaagga atccttcgat gaagagaaag gcttccag          48

<210> SEQ ID NO 22
<211> LENGTH: 48
<212> TYPE: DNA
<213> ORGANISM: Artificial Sequence
<220> FEATURE:
<223> OTHER INFORMATION: Synthetic DNA

<400> SEQUENCE: 22
gagcacgctg gaagcctttc tcttcatcga aggattcctt agcaacac          48

<210> SEQ ID NO 23
<211> LENGTH: 42
<212> TYPE: DNA
<213> ORGANISM: Artificial Sequence
<220> FEATURE:
<223> OTHER INFORMATION: Synthetic DNA

<400> SEQUENCE: 23
cgtgctcgtg aagttgcttc tgttatgaac cgtgctctag aa          42

<210> SEQ ID NO 24
<211> LENGTH: 39
<212> TYPE: DNA
<213> ORGANISM: Artificial Sequence
<220> FEATURE:
<223> OTHER INFORMATION: Synthetic DNA

<400> SEQUENCE: 24
agctttctag agcacggttc ataacagaag caacttcac          39

<210> SEQ ID NO 25
<211> LENGTH: 45
<212> TYPE: DNA
<213> ORGANISM: Artificial Sequence
<220> FEATURE:
<223> OTHER INFORMATION: Synthetic DNA

<400> SEQUENCE: 25
aattctctag agaacgctca tgatgaatct gcttacctgg ataac          45

<210> SEQ ID NO 26
<211> LENGTH: 50
<212> TYPE: DNA

```
<213> ORGANISM: Artificial Sequence
<220> FEATURE:
<223> OTHER INFORMATION: Synthetic DNA

<400> SEQUENCE: 26
cttcttcagg ttatccaggt aagcagattc atcatgagcg ttctctagag        50

<210> SEQ ID NO 27
<211> LENGTH: 49
<212> TYPE: DNA
<213> ORGANISM: Artificial Sequence
<220> FEATURE:
<223> OTHER INFORMATION: Synthetic DNA

<400> SEQUENCE: 27
ctgaagaagg aactggctaa cggtaacgat gctctgcgta acgaagatg         49

<210> SEQ ID NO 28
<211> LENGTH: 49
<212> TYPE: DNA
<213> ORGANISM: Artificial Sequence
<220> FEATURE:
<223> OTHER INFORMATION: Synthetic DNA

<400> SEQUENCE: 28
gagaacgagc atcttcgtta cgcagagcat cgttaccgtt agccagttc         49

<210> SEQ ID NO 29
<211> LENGTH: 40
<212> TYPE: DNA
<213> ORGANISM: Artificial Sequence
<220> FEATURE:
<223> OTHER INFORMATION: Synthetic DNA

<400> SEQUENCE: 29
ctcgttctcc gttctactct gctctgcgta acactccgtc                   40

<210> SEQ ID NO 30
<211> LENGTH: 39
<212> TYPE: DNA
<213> ORGANISM: Artificial Sequence
<220> FEATURE:
<223> OTHER INFORMATION: Synthetic DNA

<400> SEQUENCE: 30
ctttgaagga cggagtgtta cgcagagcag agtagaacg                    39

<210> SEQ ID NO 31
<211> LENGTH: 47
<212> TYPE: DNA
<213> ORGANISM: Artificial Sequence
<220> FEATURE:
<223> OTHER INFORMATION: Synthetic DNA

<400> SEQUENCE: 31
cttcaaagaa cgtaacggtg gtaaccatga tccgtctcgt atgaaag           47

<210> SEQ ID NO 32
<211> LENGTH: 47
<212> TYPE: DNA
<213> ORGANISM: Artificial Sequence
<220> FEATURE:
<223> OTHER INFORMATION: Synthetic DNA

<400> SEQUENCE: 32
gataacagct ttcatacgag acggatcatg gttaccaccg ttacgtt           47
```

```
<210> SEQ ID NO 33
<211> LENGTH: 45
<212> TYPE: DNA
<213> ORGANISM: Artificial Sequence
<220> FEATURE:
<223> OTHER INFORMATION: Synthetic DNA

<400> SEQUENCE: 33
ctgttatcta ctctaaacat ttctggtctg gtcaggatag atcta              45

<210> SEQ ID NO 34
<211> LENGTH: 41
<212> TYPE: DNA
<213> ORGANISM: Artificial Sequence
<220> FEATURE:
<223> OTHER INFORMATION: Synthetic DNA

<400> SEQUENCE: 34
agcttagatc tatcctgacc agaccagaaa tgtttagagt a                  41

<210> SEQ ID NO 35
<211> LENGTH: 42
<212> TYPE: DNA
<213> ORGANISM: Artificial Sequence
<220> FEATURE:
<223> OTHER INFORMATION: Synthetic DNA

<400> SEQUENCE: 35
aattcagatc ttcttctgct gataaacgta aatacggtga tc                 42

<210> SEQ ID NO 36
<211> LENGTH: 44
<212> TYPE: DNA
<213> ORGANISM: Artificial Sequence
<220> FEATURE:
<223> OTHER INFORMATION: Synthetic DNA

<400> SEQUENCE: 36
catccggatc accgtattta cgtttatcag cagaagaaga tctg               44

<210> SEQ ID NO 37
<211> LENGTH: 48
<212> TYPE: DNA
<213> ORGANISM: Artificial Sequence
<220> FEATURE:
<223> OTHER INFORMATION: Synthetic DNA

<400> SEQUENCE: 37
cggatgcatt ccgtccggct ccgggtactg gtctggtaga catgtctc           48

<210> SEQ ID NO 38
<211> LENGTH: 48
<212> TYPE: DNA
<213> ORGANISM: Artificial Sequence
<220> FEATURE:
<223> OTHER INFORMATION: Synthetic DNA

<400> SEQUENCE: 38
gatcacgaga catgtctacc agaccagtac ccggagccgg acggaatg           48

<210> SEQ ID NO 39
<211> LENGTH: 35
<212> TYPE: DNA
<213> ORGANISM: Artificial Sequence
<220> FEATURE:
```

<223> OTHER INFORMATION: Synthetic DNA

<400> SEQUENCE: 39
gtgatcgtaa catcccgcgt tctccgactt ctccg         35

<210> SEQ ID NO 40
<211> LENGTH: 36
<212> TYPE: DNA
<213> ORGANISM: Artificial Sequence
<220> FEATURE:
<223> OTHER INFORMATION: Synthetic DNA

<400> SEQUENCE: 40
cttcacccgg agaagtcgga gaacgcggga tgttac        36

<210> SEQ ID NO 41
<211> LENGTH: 40
<212> TYPE: DNA
<213> ORGANISM: Artificial Sequence
<220> FEATURE:
<223> OTHER INFORMATION: Synthetic DNA

<400> SEQUENCE: 41
ggtgaaggct tcgttaactt cgattacggt tggttcggtg    40

<210> SEQ ID NO 42
<211> LENGTH: 40
<212> TYPE: DNA
<213> ORGANISM: Artificial Sequence
<220> FEATURE:
<223> OTHER INFORMATION: Synthetic DNA

<400> SEQUENCE: 42
gtctgagcac cgaaccaacc gtaatcgaag ttaacgaagc    40

<210> SEQ ID NO 43
<211> LENGTH: 44
<212> TYPE: DNA
<213> ORGANISM: Artificial Sequence
<220> FEATURE:
<223> OTHER INFORMATION: Synthetic DNA

<400> SEQUENCE: 43
ctcagactga agctgatgct gataagactg tatggaccca tgga    44

<210> SEQ ID NO 44
<211> LENGTH: 41
<212> TYPE: DNA
<213> ORGANISM: Artificial Sequence
<220> FEATURE:
<223> OTHER INFORMATION: Synthetic DNA

<400> SEQUENCE: 44
agcttccatg ggtccataca gtcttatcag catcagcttc a    41

<210> SEQ ID NO 45
<211> LENGTH: 39
<212> TYPE: DNA
<213> ORGANISM: Artificial Sequence
<220> FEATURE:
<223> OTHER INFORMATION: Synthetic DNA

<400> SEQUENCE: 45
aattcccatg gtaaccatta ccatgctccg aacggttct     39

<210> SEQ ID NO 46
<211> LENGTH: 42
<212> TYPE: DNA
<213> ORGANISM: Artificial Sequence
<220> FEATURE:
<223> OTHER INFORMATION: Synthetic DNA

<400> SEQUENCE: 46
cacccagaga accgttcgga gcatggtaat ggttaccatg gg                         42

<210> SEQ ID NO 47
<211> LENGTH: 41
<212> TYPE: DNA
<213> ORGANISM: Artificial Sequence
<220> FEATURE:
<223> OTHER INFORMATION: Synthetic DNA

<400> SEQUENCE: 47
ctgggtgcta tgcatgtata cgaatctaaa ttccgtaact g                          41

<210> SEQ ID NO 48
<211> LENGTH: 42
<212> TYPE: DNA
<213> ORGANISM: Artificial Sequence
<220> FEATURE:
<223> OTHER INFORMATION: Synthetic DNA

<400> SEQUENCE: 48
cttcagacca gttacggaat ttagattcgt atacatgcat ag                         42

<210> SEQ ID NO 49
<211> LENGTH: 37
<212> TYPE: DNA
<213> ORGANISM: Artificial Sequence
<220> FEATURE:
<223> OTHER INFORMATION: Synthetic DNA

<400> SEQUENCE: 49
gtctgaaggt tactctgact tcgatcgtgg tgcttac                               37

<210> SEQ ID NO 50
<211> LENGTH: 37
<212> TYPE: DNA
<213> ORGANISM: Artificial Sequence
<220> FEATURE:
<223> OTHER INFORMATION: Synthetic DNA

<400> SEQUENCE: 50
gtgataacgt aagcaccacg atcgaagtca gagtaac                               37

<210> SEQ ID NO 51
<211> LENGTH: 38
<212> TYPE: DNA
<213> ORGANISM: Artificial Sequence
<220> FEATURE:
<223> OTHER INFORMATION: Synthetic DNA

<400> SEQUENCE: 51
gttatcacct tcattccgaa atcttggaac actgctcc                              38

<210> SEQ ID NO 52
<211> LENGTH: 38
<212> TYPE: DNA
<213> ORGANISM: Artificial Sequence
<220> FEATURE:
<223> OTHER INFORMATION: Synthetic DNA

```
<400> SEQUENCE: 52
ctttgtccgg agcagtgttc caagatttcg gaatgaag                              38

<210> SEQ ID NO 53
<211> LENGTH: 38
<212> TYPE: DNA
<213> ORGANISM: Artificial Sequence
<220> FEATURE:
<223> OTHER INFORMATION: Synthetic DNA

<400> SEQUENCE: 53
ggacaaagtt aaacagggtt ggccgtaatg aaagctta                              38

<210> SEQ ID NO 54
<211> LENGTH: 34
<212> TYPE: DNA
<213> ORGANISM: Artificial Sequence
<220> FEATURE:
<223> OTHER INFORMATION: Synthetic DNA

<400> SEQUENCE: 54
agcttaagct ttcattacgg ccaaccctgt ttaa                                  34

<210> SEQ ID NO 55
<211> LENGTH: 20
<212> TYPE: DNA
<213> ORGANISM: Artificial Sequence
<220> FEATURE:
<223> OTHER INFORMATION: Synthetic DNA

<400> SEQUENCE: 55
ttttcccagt cacgacgttg                                                  20

<210> SEQ ID NO 56
<211> LENGTH: 21
<212> TYPE: DNA
<213> ORGANISM: Artificial Sequence
<220> FEATURE:
<223> OTHER INFORMATION: Synthetic DNA

<400> SEQUENCE: 56
caggaaacag ctatgaccat g                                                21

<210> SEQ ID NO 57
<211> LENGTH: 36
<212> TYPE: DNA
<213> ORGANISM: Artificial Sequence
<220> FEATURE:
<223> OTHER INFORMATION: Synthetic DNA

<400> SEQUENCE: 57
taaggaggtt taaaatgtct gacgatcgtg ttactc                                36

<210> SEQ ID NO 58
<211> LENGTH: 21
<212> TYPE: DNA
<213> ORGANISM: Artificial Sequence
<220> FEATURE:
<223> OTHER INFORMATION: Synthetic DNA

<400> SEQUENCE: 58
tacgccaagg ttgttaaccc a                                                21
```

PROCESS FOR PRODUCING TRANSGLUTAMINASE

CROSS REFERENCE TO RELATED APPLICATIONS

This application is a continuation application of PCT International Application PCT/JP99/07250 filed Dec. 24, 1999, which claims priority to Japanese Patent Application No. 10-373131 filed Dec. 28, 1998, the entire contents of both documents are incorporated herein by reference.

BACKGROUND OF THE INVENTION

1. Field of the Invention

The present invention relates to a high-yield process for producing high-activity, high-purity transglutaminase by refolding denatured microorganism-derived transglutaminase by incubating denatured transglutaminase in an aqueous medium under acidic conditions and reconstituting a higher-order enzymatically active transglutaminase in an aqueous medium at a neutral pH.

2. Discussion of the Background

Transglutaminase has been widely used in the production of gel-food (such as jelly, yogurt, cheese), gel-toiletries, and modification of meat, as well as other fields. Thus transglutaminase is quite a useful industrial enzyme.

Transglutaminase (EC 2. 3. 2. 13; TGase) is an enzyme that catalyzes an acyl transfer reaction between a γ-carboxyamide group of a glutamine residue and a primary amine of a protein or a polypeptide chain. Transglutaminase isolated from a culture supernatant of a microorganism (variant of *Streptoverticillium mobaraense* in the present invention) is called microorganism-derived transglutaminase (MTG).

MTG is a monomer protein comprising 331 amino acids and has a molecular weight of 38,000 (Journal of Biological Chemistry, 268, 11565–11572, 1993). Culture conditions of the microorganism were optimized for mass production of this enzyme (Agricultural Biological Chemistry, 53, 2613, 1989). However, this microorganism was not widely used in the industrial production of MTG due to problems associated with the level of production and the production costs. Further, this enzyme is extracellularly secreted in an active state; however, in the host bacteria the protein sequence is susceptible to chemical modification by a deamidation reaction at four distinct sites. Accordingly, in a culture solution chemical modification proceeded during the secretory production and enzymes having reduced activity accumulated giving rise to a mixture of active-states in the recovered culture supernatant. In order to solve these problems, various methods for producing recombinant MTG using microorganisms such as *E. coli* have been studied (Bioscience & Bioindustry, 52, 554–561, 1994).

When the sequence of the enzyme was expressed in *E. coli* the yield of the enzyme was very low. High expression was successfully realized by fusing this enzyme with a fragment of a sequence derived from the T7 gene-10. Nevertheless, following restricted cleavage of the fusion protein, the resulting enzyme with the native sequence exhibited enzymatic activity which was approximately ⅕ of the native transglutaminase. This suggested that the enzyme obtained by this method was in an incomplete higher-order structure (Bioscience, Biotechnology, and Biochemistry, 61, 830–835, 1997). Further, restricted cleavage to liberate the native-like transglutaminase from the T7 gene-10 product fusion partner required a digestive enzyme or a chemical procedure. Thus, this method posed serious problems in that it was intricate and involved high production costs. It is therefore an object of the present invention to provide a low-cost, high-yield process by which transglutaminase can be produced for application in the various fields of food processing or other fields where applicable.

Solving these problems required developing a technology in which only the sequence of the transglutaminase is highly expressed directly from a microorganism, and a technology in which the higher-order structure harboring the enzymatic activity is completely reconstructed from the denatured enzyme recovered from the culture supernatant (refolding technology). With respect to refolding technology of proteins, it is impossible to predict the appropriate conditions for reconstructing the native state of the intended protein by examination of said native state. It is necessary that operation conditions be empirically derived for each intended protein (Advances in Protein Chemistry, 50, 1–59, 1997). The present applicant has previously succeeded in high intracellular expression of the sequence of this enzyme, which was impossible in the past, by replacing the codons inherently present in the DNA sequence with those more frequently utilized by the *E. coli* expression host (Japanese Patent Application No. 181,951/1998 filed Jun. 29, 1998, Japanese Patent Kokai Publication JP-A-11-75,876, published Mar. 23, 1999; hereinafter referred to as a "prior invention"). Codon optimization significantly increased the copy number of the plasmid encoding the transglutaminase gene further amplifying the expression of this enzyme. Accordingly, it is now possible to obtain the transglutaminase in a denatured state in large quantities and to investigate the refolding technology of the enzyme for the first time.

SUMMARY OF THE INVENTION

The present invention aims to develop a method of refolding recombinant microorganism expressed transglutaminase from a denatured state to reconstitute enzymatic activity. The ambition of this method is to construct a less costly industrial process for expressing the enzyme and to provide a means of producing transglutaminase having an enzymatic activity that is equal to the native transglutaminase (namely transglutaminase activity).

In order to solve the aforementioned problems and attain the aim of the present invention, the inventors have found that transglutaminase having an enzymatic activity can be produced with high efficiency by subjecting denatured transglutaminase to minimally the following steps (a) and (b):

(a) a step for forming an intermediate structure in which said enzyme in the denatured state is allowed to react in an aqueous medium under acidic conditions; and (b) a step for forming a higher-order structure exhibiting enzymatic activity by bringing the aqueous medium having said intermediate structure to a neutral pH region.

In another embodiment of the invention, the process for producing transglutaminase having an enzymatic activity comprises:

(a) incubating a denatured transglutaminase in an acidic aqueous medium; and (b) adjusting the pH of said aqueous medium to a neutral pH.

The enzyme having the intermediate structure obtained in step (a) has the transglutaminase enzymatic activity, which is substantially lower than that of native transglutaminase when comparing it to the enzyme present in nature. For example, the enzymatic activity is typically 15 to 25 U/mg as compared to greater than 30 U/mg observed for the native state.

Additional objects of the invention will be set forth in the Detailed Description which follows.

1. MTG standard (4 μg);
2. All fractions of disrupted cell of pUC19/JM109 (negative control);
3. All fractions of disrupted cell of pUCTRPMTG-02/JM109;
4. Centrifugation supernatant fraction of lane 3; and
5. Centrifugation precipitate fraction of lane 3.

Figure 4:
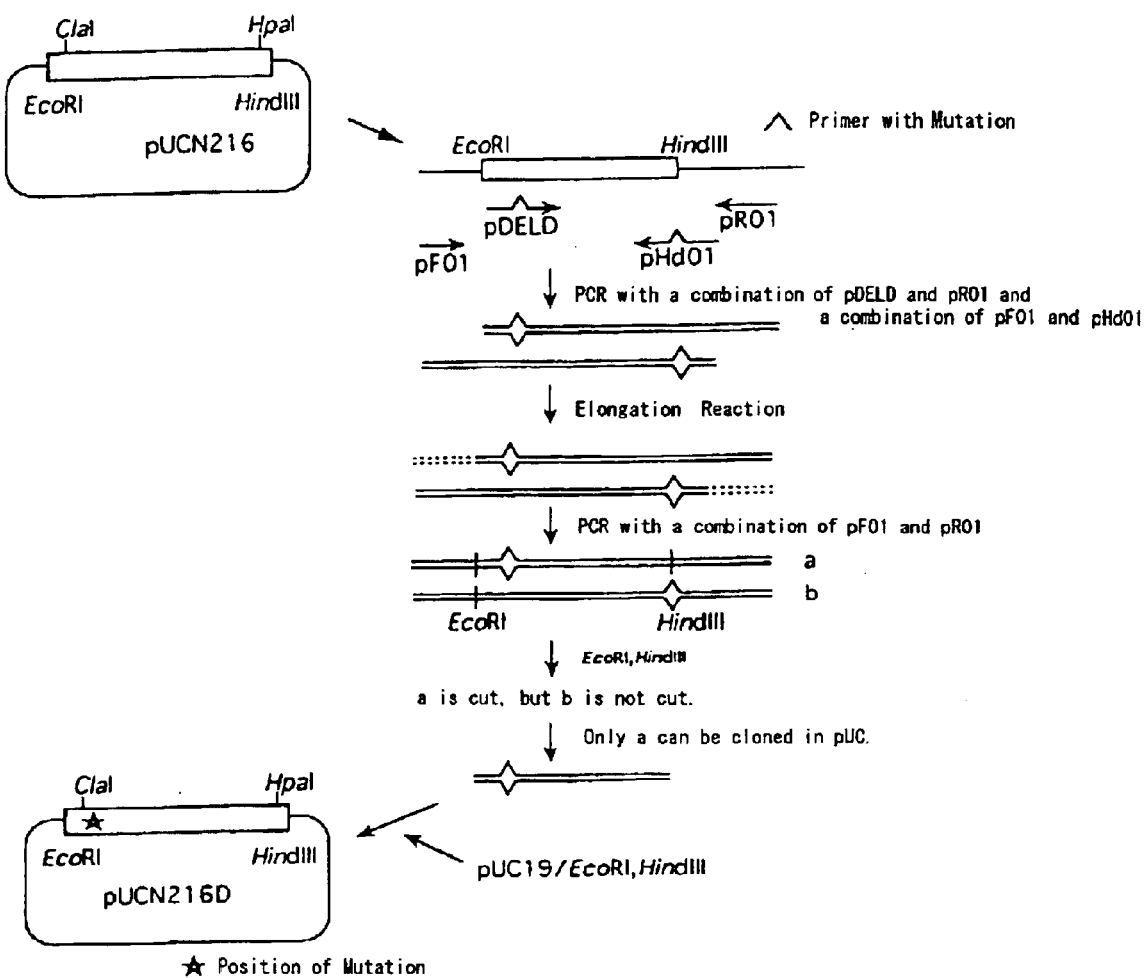

FIG. 4. Construction of pUCN216D plasmid.

Figure 5:
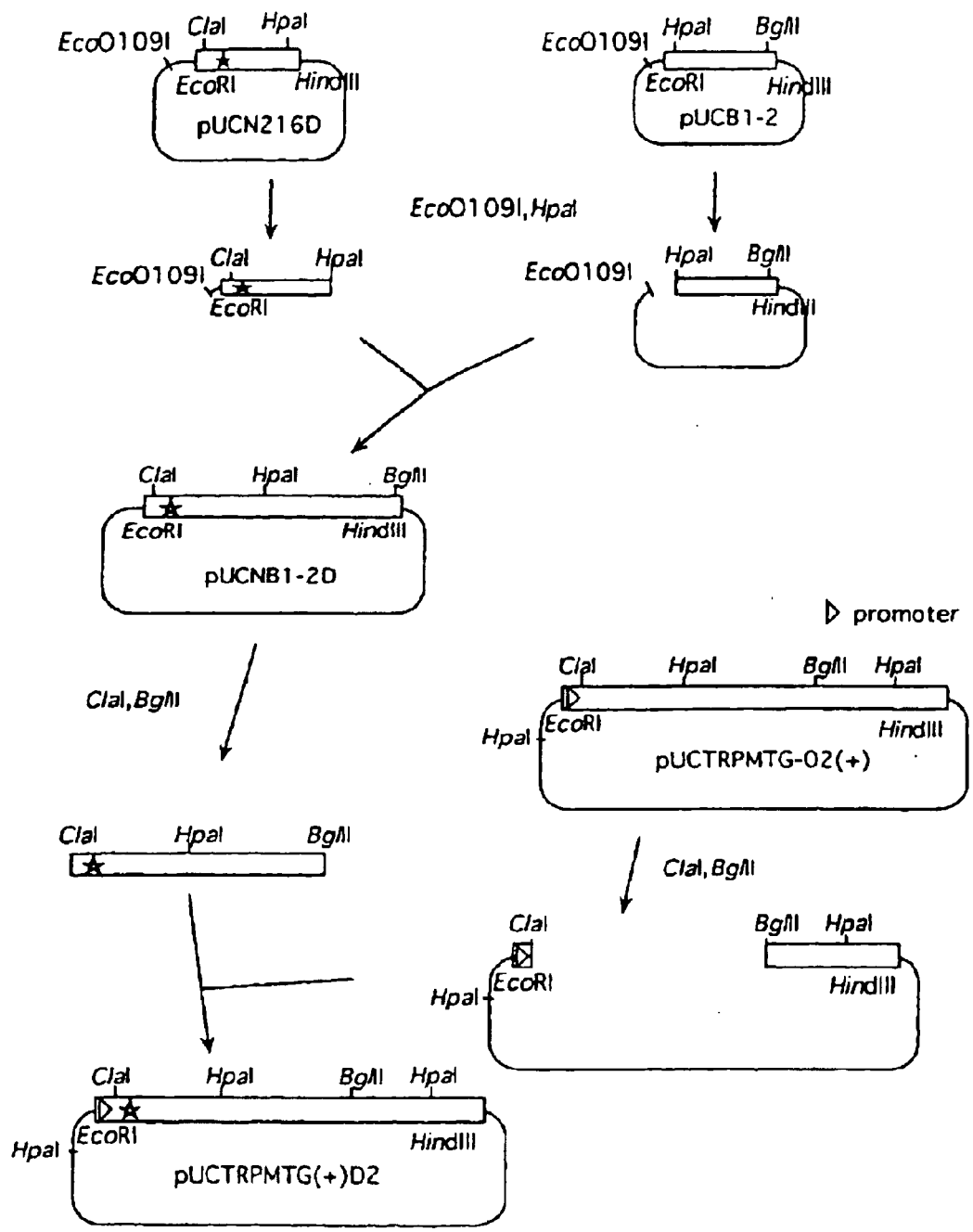

FIG. 5. Construction of the MTG expression plasmid pUCTRPMTG(+)D2.

FIG. 6. MTG N-terminal sequence of pUCTRPMTG(+)D2 (aspartic acid (GAT) deletion).

FIG. 7. MTG N-terminal amino acid residue as a function of expression source.

Figure 8:
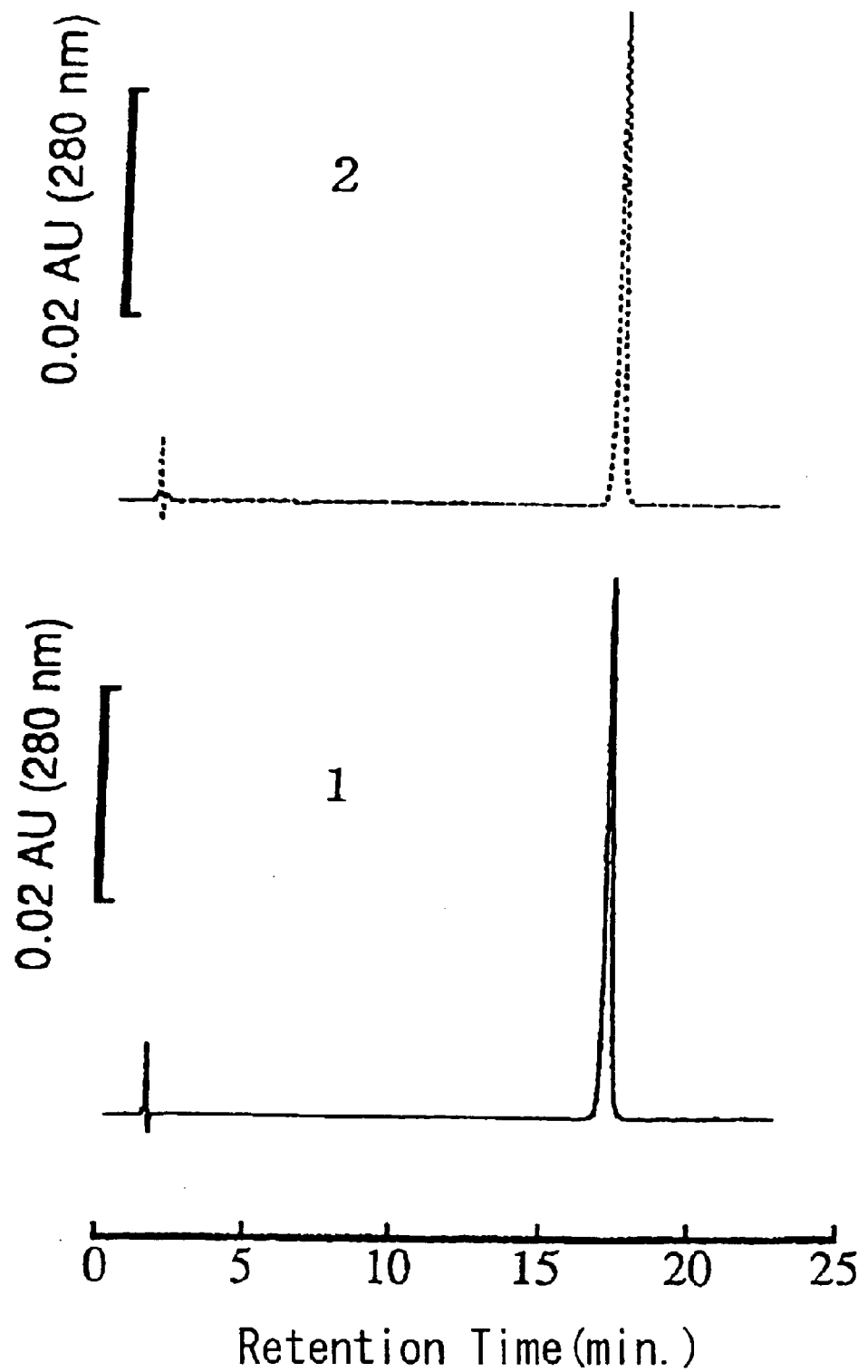

FIG. 8. Reverse phase HPLC of 8 μg recombinant-type MTG (1) and natural-type transglutaminase (2).

Reverse phase HPLC experiments were conducted under the following conditions:

Column: Vydac 214TP5410;

Eluent: A: 0.1% TFA (trifluoroacetic acid);
B: 0.1% TFA, 80% acetonitrile;

Elution program: 1 ml/min

| Time (min) | A (%) | B (%) |
|---|---|---|
| 0 | 70 | 30 |
| 20 | 50 | 50 |
| 25 | 0 | 100 |
| 28 | 0 | 100 |

Figure 9:
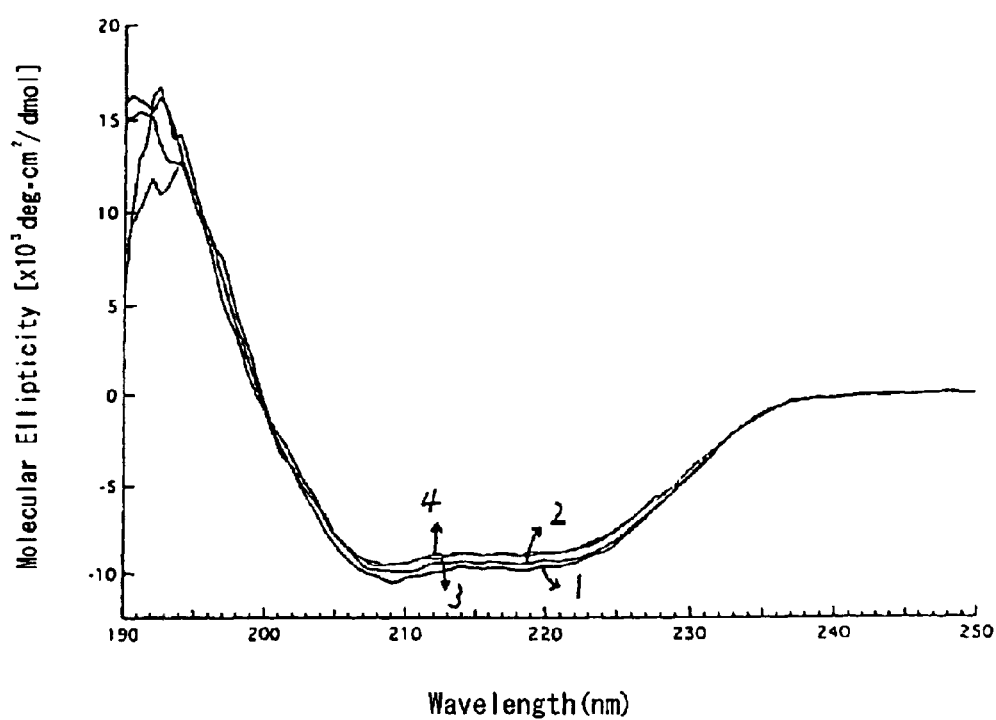

FIG. 9. CD (circular dichroism) spectrum of natural-type transglutaminase and recombinant-type MTG.

The CD spectrum of four specimens in Example 1 was measured at 20° C. using AVIV Model 62 ADS (manufactured by HART SCIENTIFIC) and a 1 mm cell.

Specimen Nos. 1 to 4 in the drawing are as follows:

| Specimen Number | Transglutaminase | pH value of buffer | Concentration of Transglutaminase |
|---|---|---|---|
| 1 | natural type | 4.0 | 3.22 mg/ml |
| 2 | natural type | 5.8 | 3.20 |
| 3 | recombinant type | 4.0 | 1.81 |
| 4 | recombinant type | 5.8 | 1.69 |

Figure 10:
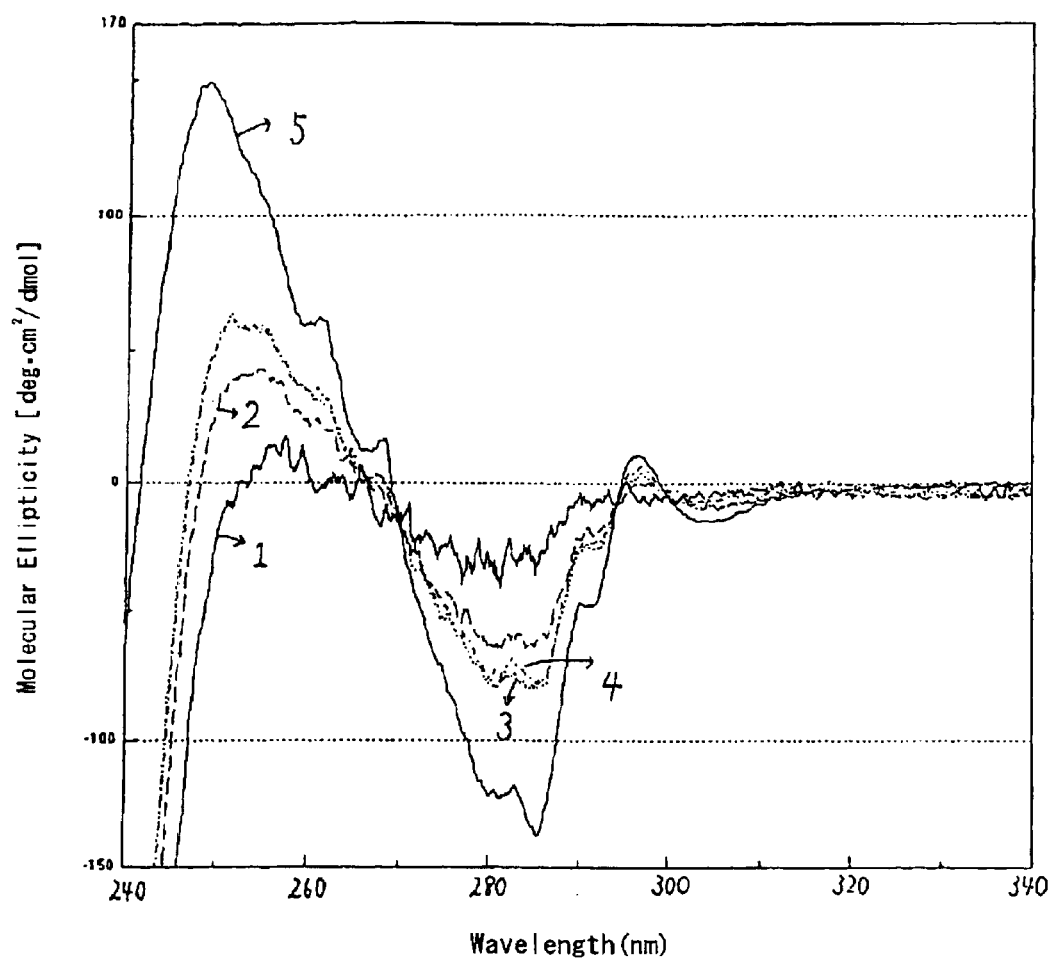

FIG. 10. CD spectrum of a native-state and an intermediate-state during structural construction of recombinant-type transglutaminase obtained in Example 12.

1. 0 to 10 min. after dilution;
2. 10 to 60 min. after dilution;
3. 60 to 160 min. after dilution;
4. 170 to 270 min. after dilution; and
5. purified recombinant-type transglutaminase.

Figure 11:
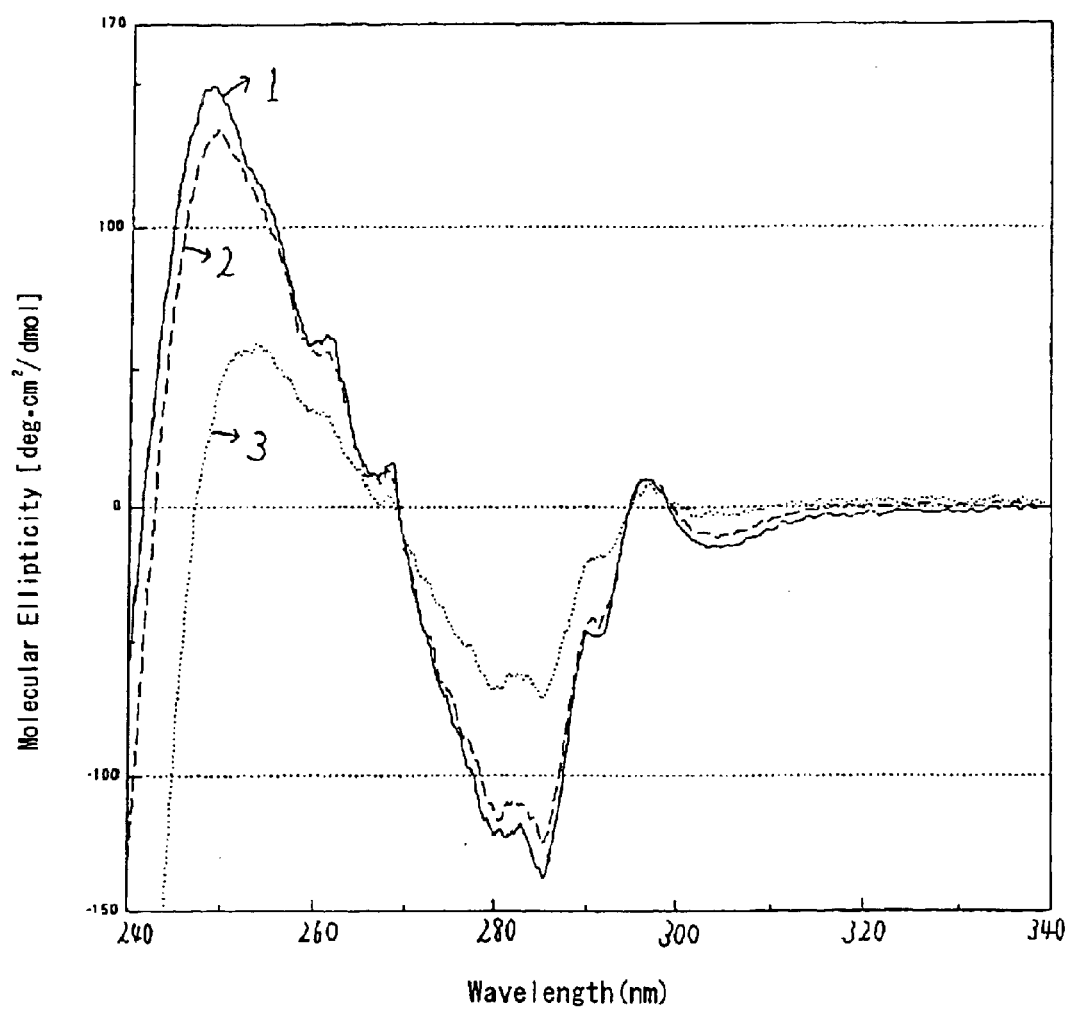

FIG. 11. CD spectrum of a native-state and an intermediate-state during structural construction of recombinant-type transglutaminase obtained in Example 12.

1. purified recombinant-type transglutaminase;
2. purified recombinant-type transglutaminase adjusted to pH 4.2 in 0.16 M urea; and
3. transglutaminase after 26 hours from dilution in a denatured state.

Figure 12:
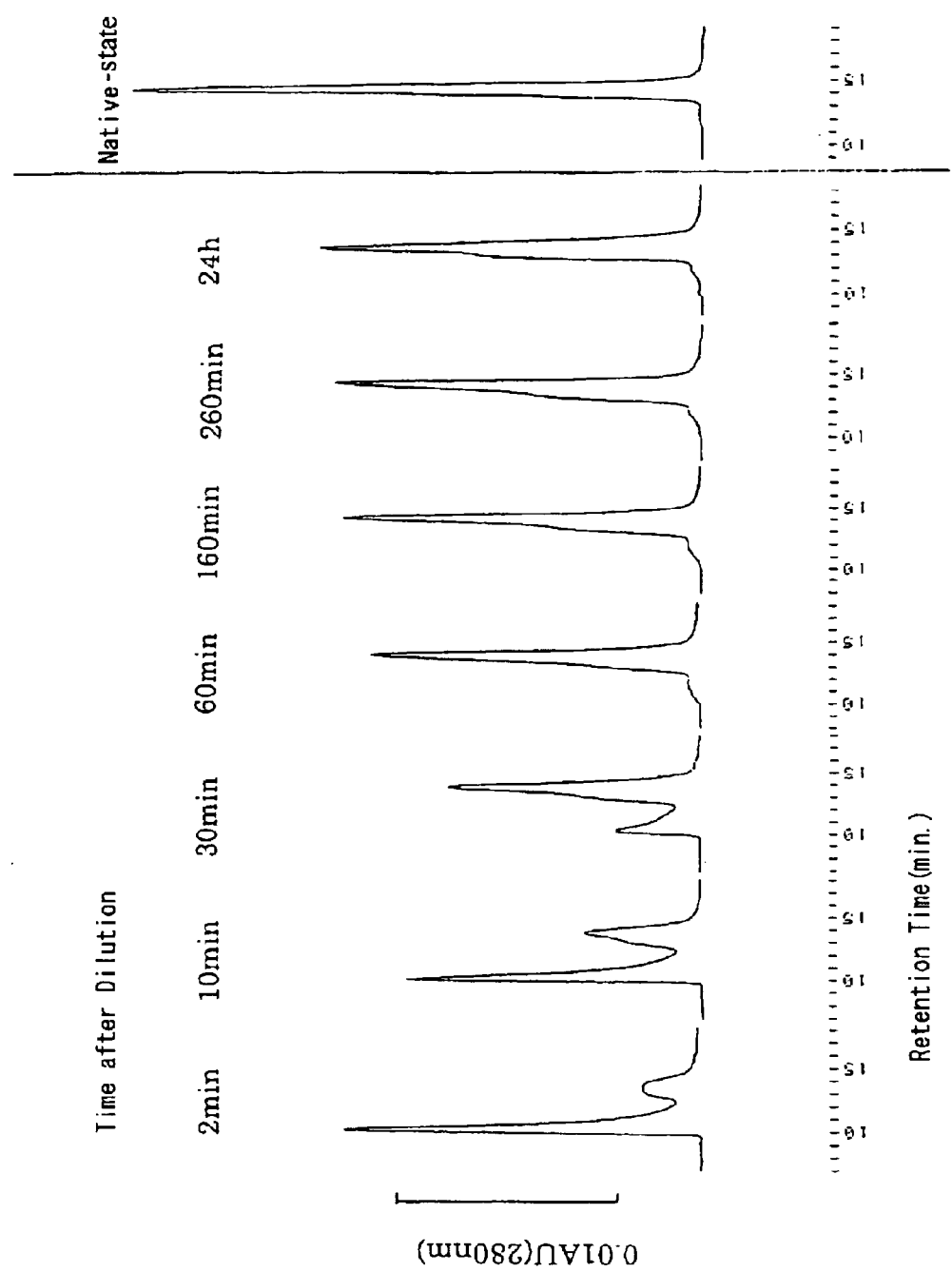

FIG. 12. Chromatogram of gel filtration analysis on a native-state and an intermediate-state during structural construction of recombinant-type transglutaminase obtained in Example 13.

Figure 13:
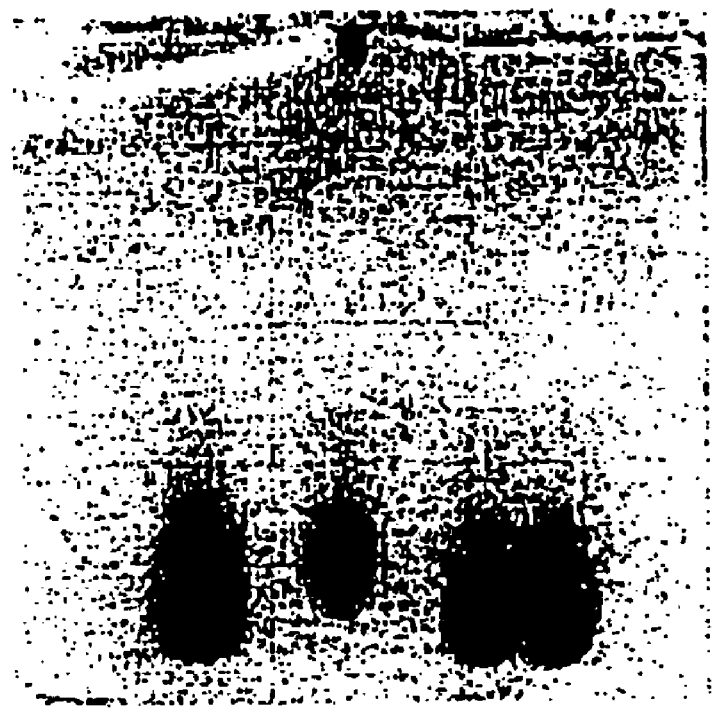

FIG. 13. Native-PAGE of a native-state and an intermediate-state during structural construction of recombinant-type transglutaminase obtained in Example 16.

1. purified recombinant-type transglutaminase;
2. transglutaminase after 26 hours from dilution in a denatured state;
3. purified recombinant-type transglutaminase adjusted to pH 4.2 in 0.16 M urea; and
4. same as 3.

DETAILED DESCRIPTION OF THE INVENTION

The present invention promulgates a refolding process by which high-activity transglutaminase can be efficiently produced from the denatured form of the enzyme. Transglutaminase having an enzymatic activity can be produced by subjecting said denatured transglutaminase to:

(a) a step for forming an intermediate structure (in structural construction of the state having the transglutaminase enzymatic activity) in which the denatured enzyme is allowed to react in an aqueous medium under an acidic condition; followed by (b) a step for forming a higher-order structure in which the enzyme having the intermediate structure in the structural construction comes to have the transglutaminase enzymatic activity in an aqueous medium under a neutral pH region.

That is, the present invention is a process for producing transglutaminase, which contains at least the foregoing steps (a) and (b), especially in the refolding procedure. However, the present invention has the following additional contents.

1. The process, wherein in step (a), a thiol group of a cysteine residue in the molecule of the enzyme is in a free form. In case of a dimer in which two molecules are coupled by a cysteine residue moiety, it is preferable that a thiol group is rendered in a free form by reduction arising through the inclusion of a reducing agent, for example dithiothreitol (DTT), 2-mercaptoethanol (β-ME), and tris-(2-carboxyethyl)phosphine (TCEP). The enzyme in the dissolved, denatured state is diluted under an acidic condition forming an intermediate structure (in structural construction for the state having the transglutaminase enzymatic activity).

2. In the above process, wherein the denatured state of the enzyme is generated by inclusion of a protein denaturant in the aqueous medium.

It is preferable that transglutaminase as a starting material is dissolved well in the aqueous medium, and a protein denaturant can be used as its solubilizer (auxiliary substance for dissolution). In this case, examples of the protein denaturant can include urea, guanidine hydrochloride and thiocyanate. The concentration thereof usually varies with the concentration used to denature a protein or the type of the denaturant. For example, when urea is used as the denaturant, it can be used in an amount of 4 to 10 M or the like. The dilution may be conducted directly or stepwise.

3. The process, wherein in step (a), the acid solution of the denatured enzyme is diluted under an acidic condition at a low temperature, preferably at 15° C. or less, and the concentration of thus diluted protein is not more than 10 mg/ml.

The dilution degree is 5-fold or more, preferably 10-fold or more, more preferably 50-fold to 400-fold or greater. The dilution may be conducted in multiple stages. Further, when the concentration before the dilution and the concentration after the dilution are indicated in terms of the concentration of the following denaturant used in the dilution, it is desirable that in case of urea, the concentration of 4 to 10 M or so is adjusted to the concentration of 0.01 to 0.5 M or so by the dilution.

It is preferable that step (a) is conducted at a low temperature. It is especially preferable that the dilution is conducted at a low temperature. For example, it can be conducted at a low temperature of 15° C. or less, preferably 3 to 10° C.

4. The process, wherein in step (b), said neutral region is provided by increasing the pH value of the enzyme solution obtained in step (a) to a pH value between 5.8 and 8.5 by addition of an alkaline solution. An example of which is sodium hydroxide.

5. The process, wherein in step (b), the aqueous medium contains an accelerator for forming a higher-order structure having an enzymatic activity.

Step (b) includes a stage of adjusting the pH value of the aqueous medium to a neutral region. It is advisable to use an accelerator to facilitate the formation of the desired higher-order structure, especially before the pH value is increased. In this case, a low-molecular weight compound is preferable as the accelerator. Examples thereof include inorganic salts such as calcium chloride and strontium chloride, organic acid salts such as sodium acetate and sodium propionate, amino acid salts such as arginine hydrochloride, polyols such as polyethylene glycol, organic solvents such as DMSO and DMF, and surfactants such as CHAPS.

6. In the above process, which includes an additional step (c) of separating inactive enzyme(s) in the aqueous medium as aggregate(s) after step (b) by centrifugation.

7. In the above process, wherein the intermediate structure in the structural construction obtained in step (a) has the following properties (a) to (b):
   (a) specific activity of 15 to 25 U/mg provided through measurement of transglutaminase activity by the hydroxamate method;
   (b) a molecular ellipticity which is 30 to 70% of that of a native state in a CD spectrum of a near ultraviolet region;
   (c) a molecular weight of 36,000 to 40,000 as measured by SDS-polyacrylamide gel electrophoresis; and
   (d) lower mobility than that of a native state in native-polyacrylamide gel electrophoresis with a His-Mes buffer system of pH 6.1.

In the SDS-polyacrylamide gel electrophoresis, it is preferable to provide a molecular weight standard equal to that of a native state, namely, approximately 38,000. While transglutaminase activity can be measured by the known hydroxamate method (refer to, for example, Bioscience, Biotechnology, and Biochemistry, 61, 830–835, 1997).

Therefore, a preferable example of the present invention for the production of native transglutaminase having an enzymatic activity from denatured transglutaminase (MTG) is by a refolding method comprising the following steps (a') and (b'):

(a') a step of adjusting the pH value of an aqueous medium, containing solubilized and denatured microorganism-derived transglutaminase in which a thiol group of a cysteine residue (Cys) as an active residue is in a free form to an acidic region, and diluting the solution with an acid buffer, containing a dilute denaturant, preferably to 50 to 400 times or more to obtain a transglutaminase having the intermediate structure (state) in the structural construction of the native state; and (b') a step of adding an alkaline solution to the enzyme-containing solution having the intermediate structure (state) in the structural construction either directly or after adding a low molecular weight compound of accelerating the structural construction to increase the pH value to a neutral region of 6 to 7 or the like and to accelerate the formation of the higher-order structure of the enzyme or to form the higher-order structure, and separating, as required, an inactive fraction that does not undergo the structural construction as an aggregate.

The embodiments to carry out the present invention are described in detail below. Especially, refolding of a denatured enzyme which is obtained by culturing recombinant *E. coli* is specifically described as a preferable example. However, the present invention is not limited thereto.

The starting material to be treated in the present invention includes denatured transglutaminase, preferably transglutaminase having no higher-order structure of a native state, such as microorganism-derived denatured transglutaminase (MTG) and that substantially does not show an enzymatic activity, and an enzyme having a sequence that can finally exhibit transglutaminase activity.

To describe in more detail, a sequence of native transglutaminase comprises 331 amino acids starting from an aspartic acid residue (1st) in the N-terminus and ending with a proline residue (331st) in the C-terminus. Such a protein is naturally included in the starting material of the present invention. It further includes a protein comprising 330 amino acids from the 2nd amino acid residue to the 331st amino acid residue (1st aspartic acid residue is deleted), and a protein in which one or more amino acid residues are bound to the N-terminus and/or the C-terminus and which substantially does not exhibit a transglutaminase activity but exhibits or can possibly exhibit this activity through transfer to a higher-order structure. The protein having the amino acid sequence in which one or more amino acids are deleted, replaced and/or added or inserted and which exhibits or can possibly exhibit a transglutaminase activity by the process of the present invention is included in the starting material of the present invention.

As a typical example of the starting material used in the present invention, a culture containing a denatured enzyme that is obtained by incubating a microorganism having inserted therein a microorganism-derived transglutaminase gene, for example, recombinant *E. coli* can be mentioned (refer to the prior invention by the present applicant and the production example to be described later in the examples). A protein having a sequence which can finally exhibit a transglutaminase activity, despite having a part of the microorganism-derived transglutaminase gene changed and a part of the amino acid sequence expressed deleted and/or replaced (by one or more amino acid residues) and/or one or more amino acids added or inserted in one or multiple sites, can also be used in the present invention as a starting material.

When *E. coli* is used as a production host, microorganism-derived transglutaminase is mostly accumulated in cells as insoluble granules. Thus, the granules can be used as a starting material. In this case, the insoluble granules of microorganism-derived transglutaminase recovered by an ordinary method are preferably solubilized in an aqueous medium. It is advisable that the granules are suspended in a 1 mM ethylenediaminetetraacetic acid (EDTA) aqueous solution and then solubilized using a protein denaturant such as urea or guanidine hydrochloride. Thiocyanate (or other chaotropic agents) can also be mentioned as a denaturant for solubilization.

The concentration of urea and the concentration of guanidine hydrochloride may be 7 to 10 M or the like, and 4 to 7 M or the like, respectively which are generally required for denaturation of proteins. The concentration of microorganism-derived transglutaminase is not particularly limited. A higher concentration is preferable for the subsequent procedure, for example 10 to 100 mg/ml or so.

When a disulfide bond found in, for example, a dimer is reduced, it is advisable to add a reducing agent to such an aqueous solution. In this case, it is advisable that a reducing agent, for example, dithiothreitol (DTT) is immediately added at a concentration of 20 mM to the aqueous solution and to adjust the pH value to 7.5. The mixture is then stirred at 37° C. for approximately 20 hours for solubilization.

Subsequently, a suitable amount of an acid such as hydrochloric acid is added to the thus-obtained solution containing microorganism-derived transglutaminase dissolved therein to adjust the pH value to between 2 and 7, preferably between 3 and 5, more preferably between 3.5 and 4.5. The solution is diluted with the same concentration of a buffer containing a denaturant and a reducing agent at the same pH value or approximately the same pH value to adjust the concentration to between 10 and 100 mg/ml, preferably between 20 and 80 mg/ml or the like. Such a dilution procedure under the acidic condition is preferable for expediting the formation of the higher-order structure. A lower treating temperature is preferable. It is advisable to conduct the treatment at 0 to 15° C., preferably at 3 to 10° C. or the like.

The above-obtained solution is diluted with a buffer containing 5 to 50 mM, preferably 15 to 25 mM of sodium acetate at pH of 3 to 5, preferably 3.5 to 4.5 and previously cooled to between 3 and 10° C. to adjust the protein concentration to between 0.2 and 4 mg/ml and the urea concentration to between 0.01 and 0.5 M, whereby the denatured enzyme can be led to an intermediate structure (state) in the structural construction. This intermediate state is a kinetic intermediate state that is effectively observed for the first time by adjustment of a solvent atmosphere and dilution under an acidic condition. It is not a state that is easily introduced at equilibrium from the native state (refer to Examples 11 to 16 to be described later).

The dilution of the denatured enzyme can also be carried out in multiple stages. The total dilution is preferably 50-fold to 400-fold or so. When the denaturant is used and the dilution is expressed in terms of the concentration of the denaturant, it is advisable that in case of urea, the concentration of 4 to 10 M or the like is adjusted to the concentration of 0.01 to 0.5 M or the like by the dilution.

For obtaining the intermediate structure (intermediate state) in the structural construction suited for the refolding in the dilution under the acidic condition, it is advisable to retain the enzyme for a long period of time, for example, 0.5 hour or more, preferably 1 hour or more, more preferably 1.5 hours or more.

The resulting intermediate structure (state) is different from the native structure (state), as shown in Examples 11 to 16, to be described later. The "native" transglutaminase can be obtained in good efficiency by selecting preferable dilution conditions in the present invention.

The formation of the intermediate state can be identified by comparing peak areas of microorganism-derived transglutaminase detected by reverse phase high-performance liquid chromatography (HPLC) using, for example, Vydac214TP54 (4.6 $\phi \times 250$ mm, SEPARATIONS GROUP) and peak areas thereof detected by high-performance gel filtration chromatography using, for example, Superdex-75HR 10/30 (10 $\phi \times 300$ mm, Amersham-Pharmacia-Biotech). In this case, the enzymatic activity of the intermediate state measured by the method described in the literature (Bioscience, Biotechnology, and Biochemistry, 61, 830–835, 1997) is low. For example, it is 10 to 20 U/mg or the like in terms of specific activity, and is much lower than enzymatic activity (approximately 30 U/mg) of a native state. The enzyme having such an enzymatic activity, or its fraction, is included in the enzyme having the "intermediate structure in the structural construction" obtained in step (a) in the present invention. Accordingly, when MTG having such a low enzymatic activity is formed (without including a step of collecting the same), step (a) in the present invention is completed.

It is also possible to form the intermediate structure (state) by gel filtration chromatography or dialysis instead of the dilution. However, gel filtration chromatography or dialysis is undesirable because it may lead to a decrease in recovery rate or enzymatic activity (specific activity) of the enzyme protein compared with the dilution. When the low enzymatic activity is obtained, the enzyme in step (a) can be subjected to step (b) in the present invention without the need of separating the same.

Successively, it is advisable to treat, in step (b), the thus-obtained solution containing the enzyme with the intermediate state under a neutral pH region. In this case, it is possible to increase the pH value to the neutral region while maintaining the enzyme solution at a low temperature, for example, 15° C. or less, preferably 3 to 10° C. With respect to a method for providing the neutral pH region, it is preferable that a supernatant containing only microorganism-derived transglutaminase with the structural construction completed can be recovered, preferably by adding an alkaline solution to the enzyme solution to increase the pH value to between 5.8 and 8.5, preferably between 6 and 7, and removing the resulting precipitate through centrifugation. Accordingly, this method is quite advantageous because an inactive enzyme in which the structural construction has not been attained can easily be separated as an aggregate. When the structure having the desired enzyme activity is obtained even partially (without including a collection step), step (b) in the present invention is completed.

The enzymatic activity of the supernatant is increased to approximately 30 U/mg which is equal to that of a native state, and elution peak profiles measured by various HPLC's, spectroscopic properties and thermal stability agree with those of native microorganism-derived transglutaminase either completely or substantially. In view of the foregoing, it is found that the refolding from the denatured protein to the native enzyme is completed. Separation and purification steps of the enzyme can easily be conducted by utilizing known methods for separating and purifying transglutaminase and other enzymes.

Further, when the pH value of the intermediate state is increased, the structural construction from the intermediate state to the native state can be expedited by adding thereto a low molecular weight compound as an accelerator in advance. For example, it is considered that a divalent metal salt such as calcium chloride (CaCl$_2$) in an amount of 0.01 to 10 mM expedites a local construction of a nucleus in structural transfer of the intermediate state to the native state. Further, an inorganic salt such as strontium chloride other than calcium chloride can be employed. Still further, 0.1 to 2 M of an organic acid salt such as sodium acetate or sodium propionate, 0.1 to 2 M of an amino acid salt such as arginine hydrochloride, 10 to 40% of an organic solvent such as dimethyl sulfoxide (DMSO) or dimethylformamide (DMF), 1 to 10% of polyol such as polyethylene glycol, 1 to 50 mM of a surfactant such as CHAPS is considered to change properties of a buffer to control aggregation of an enzyme produced during structural transfer to the native state and to improve a recovery rate of the enzyme protein.

The thus-obtained transglutaminase has quite a high purity, and it is not difficult in particular to separate and isolate the same. It can easily be conducted by an ordinary or known enzyme (transglutaminase) isolation method.

According to the refolding method described above (used in the present invention), transglutaminase having substantially the same enzymatic activity as native transglutaminase, namely transglutaminase activity, can be produced industrially in quite high purity from the enzyme obtained in the denatured state from a recombinant microorganism. Since transglutaminase obtained in the present invention has an activity that is substantially the same as that of native transglutaminase and has quite a high purity, there is no need to purify the same. It can directly be used, like native transglutaminase, in the field of food processing or other fields where applicable.

Especially, through dilution in an acid solution, preferably dilution in a state where the pH value is almost constant and the subsequent adjustment to a neutral region, the formation of the desired higher-order structure can be accelerated with good efficiency via an intermediate structure in the structural construction of the state having the enzymatic activity from denatured transglutaminase to produce the enzyme having the desired enzymatic activity.

The intermediate product having the intermediate structure in the structural construction described above is also provided.

Having generally described this invention, a further understanding can be obtained by reference to certain specific examples which are provided herein for purposes of illustration only, and are not intended to be limiting unless otherwise specified.

EXAMPLES

The present invention is illustrated specifically by referring to the following production example and specific examples.

A culture obtained by incubating E. coli having introduced therein DNA encoding microorganism-derived transglutaminase in 2×YT medium and accumulating intracellularly microorganism-derived transglutaminase as insoluble granules was produced as follows for using the same as a starting material. The details thereof are described in the Japanese Patent Application No. 181,951/1998 filed Jun. 29, 1998, Japanese Patent Kokai Publication JP-A-11-75,876 published Mar. 23, 1999 on the prior invention by the present applicant described above and the whole contents in the specification thereof are also incorporated by reference in the present specification.

As MTG is intracellularly accumulated as insoluble granules, it was contained in a centrifugation precipitate fraction of a disrupted cell solution as described below. In Examples to follow, the centrifugation precipitate fraction was used as granules and no transglutaminase activity was detected in the granules.

<Mass Production of MTG in E. coli>

<1> Construction of MTG Expression Plasmid pTRPMTG-01

In consideration of the frequency of using codons of E. coli or yeast, MTG gene was already completely synthesized (refer to the Japanese Patent Kokai Publication JP-A-5-199, 883). However, this gene sequence was not optimum for expression in E. coli. That is, codons of 30 arginine residues present were all minor AGA codons. Therefore, approximately 200 bases from the N-terminus of MTG gene were re-synthesized to be optimum for expression of E. coli.

Figure 1:
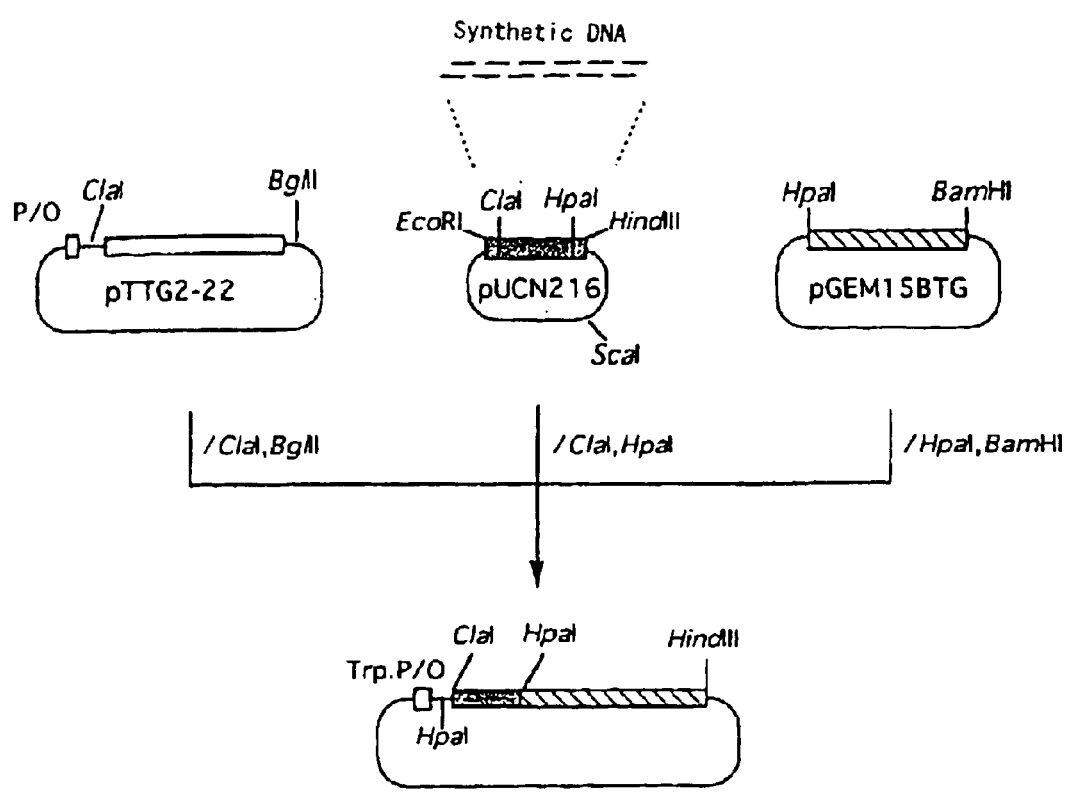
FIG. 1. Construction of the MTG expression plasmid, pTRPMTG-01.

The Trp promoter was used for transcribing MTG gene. The Trp promoter is easily induced by temporally supplementing tryptophan deficient growth media deficient with tryptophan. In plasmid pTTG2-22 (refer to the Japanese Patent Kokai Publication JP-A-6-225,775) in which red sea bream-transglutaminase (TG) gene has been highly expressed, Trp promoter is used, and an upstream sequence of red sea bream TG gene is so designed that a foreign protein is highly expressed in E. coli.

pTRPMTG-01 was constructed, as shown in FIG. 1, by replacing a portion from ClaI site to BglII site downstream of Trp promoter in red sea bream TG expression plasmid pTTG2-22 (refer to the Japanese Patent Kokai Publication JP-A-6-225, 775) with (by) a synthetic DNA gene ClaI/HpaI fragment and an HpaI/BamHI fragment (small) of pGEM15BTG (refer to the Japanese Patent Kokai Publication JP-A-6-30,771).

The synthetic DNA gene ClaI/HpaI fragment is a gene sequence having a sequence from ClaI site downstream of Trp promoter in pTTG2-22 to translation initiation codon and 216 bases from the N-terminus of MTG gene. With respect to the MTG structural gene portion, the base sequence was determined to be optimum for expression of E. coli in view of the frequency of codon usage of E. coli. However, for removing formation of a higher-order structure of mRNA, the third letter in degenerated codon in a region encoding the N-terminus portion was changed to a codon rich in adenine or uracil so that the same base was not repeated as much as possible in the consideration.

The, synthetic DNA gene ClaI/HpaI fragment was designed to have EcoRI and HindlII in the end. The designed gene was divided into portions each having approximately 40 to 50 bases such that +chain and −chain overlapped with each other, and 12 DNA's corresponding to the respective sequences were synthesized (SEQ ID No: 3 to 14). The 5'-terminus of this synthetic DNA was phosphorylated, and synthetic DNA's to be paired were annealed, and then ligated. Subsequently, acrylamide gel electrophoresis was conducted, and DNA having a desired size was cut out, and inserted (incorporated) into EcoRI/HindlIII site of pUC19. The sequences were identified, and the correct one was designated pUCN216. From this pUCN216, a ClaI/HpaI fragment (small) was cut out, and used for construction of pTRPMTG-01.

<2> Construction of MTG Expression Plasmid pTRPMTG-02

Figure 2:
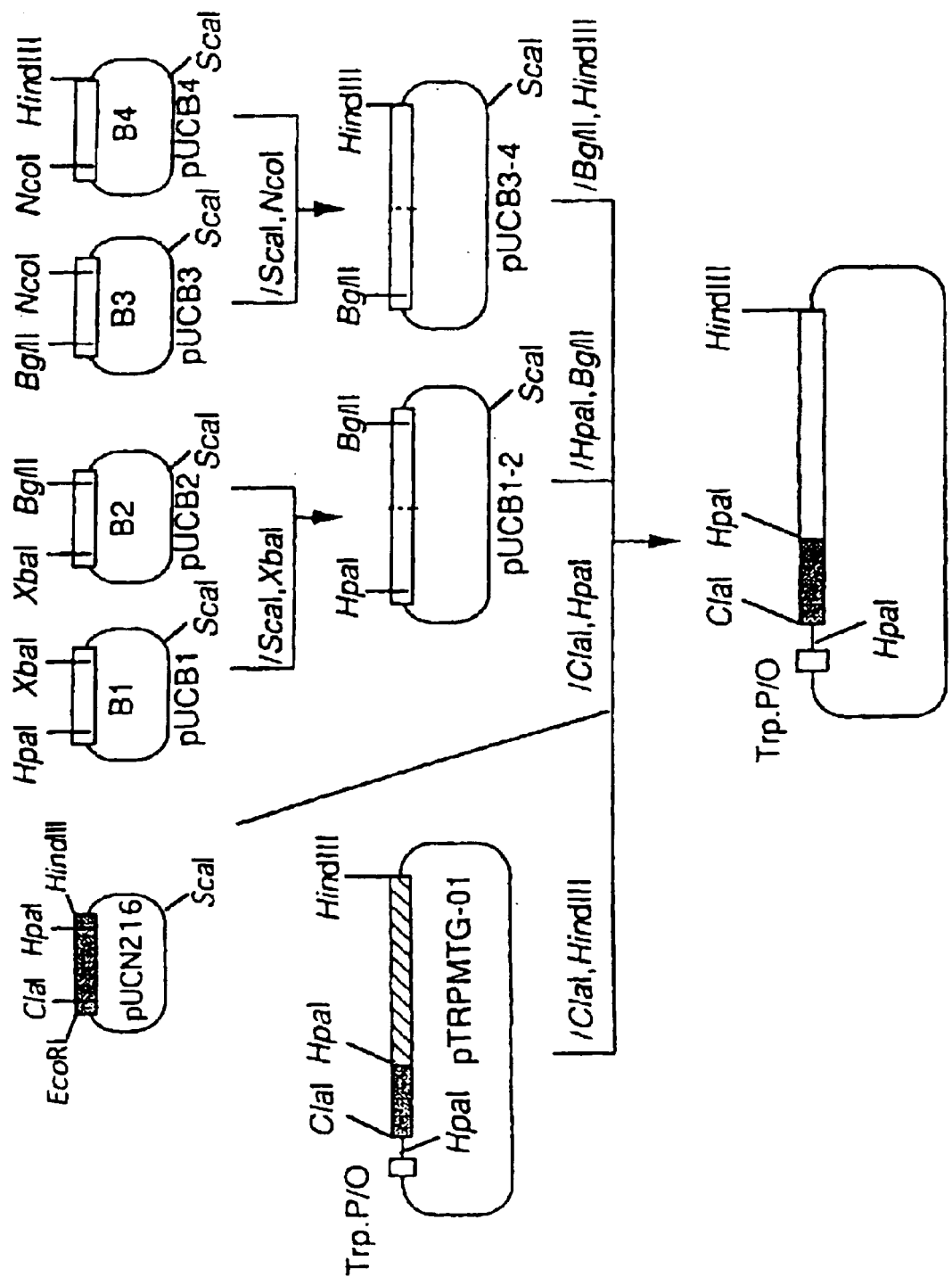
FIG. 2. Construction of the MTG expression plasmid, pTRPMTG-02.

Since E. coli JM109 having pTRPMTG-01 did not highly express MTG, a portion (777 bases) other than the modified portion of the N-terminus of MTG gene was also modified for E. coli. It is difficult to synthesize 777 bases at a time. Therefore, after a base sequence was determined in view of the frequency of codon usage of E. coli, it was synthesized by being divided into four blocks (B1, B2, B3, and B4) each having approximately 200 bases. Each block was designed to have EcoRI and HindIII in the ends. The designed gene was divided into sequences each having approximately 40 to 50 bases such that +chain and −chain overlapped with each other. With respect to DNA's corresponding to the respective sequences, a total of 40 DNA's (10 DNA's for each block) were synthesized (SEQ ID No: 15 to 54). The 5'-terminus of this synthetic DNA was phosphorylated, and synthetic DNA's to be paired were annealed, and then ligated. Subsequently, acrylamide gel electrophoresis was conducted, and DNA having a desired size was cut out, and inserted into EcoRI/HindIII site of pUC19. The base sequences were identified (confirmed), and the correct ones were designated pUCB1, pUCB2, pUCB3 and pUCB4, respectively. Then, as shown in FIG. 2, pUCB1-2 and pUCB3-4 were produced by ligating B1 with B2 and B3 with B4. Further, from pTRPMTG-01, pUCN216, pUCB1-2 and pUCB3-4, pTRPMTG-02 was constructed. The base sequence including high expression MTG gene present on pTRPMTG-02 is shown in SEQ ID No: 1.

<3> Construction of MTG Expression Plasmid pUCTRPMTG-02 (+), (−)

Since *E. coli* JM109 having this pTRPMTG-02 did not highly express MTG either, the plasmid was multi-copied. An Eco0109I fragment (small) containing Trp promoter of pTRPMTG-02 was blunt-ended, and then inserted into HindII site of pUC19, a multi-copy plasmid to construct a plasmid in which lacZ promoter and Trp promoter were the same (pUCTRPMTG-02 (+)) or opposite (pUCTRPMTG-02 (−)).

<4> Expression of MTG

*E. coli* JM109 transformed with pUCTRPMTG-02 (+) and pUC19 was incubated in 3 ml of 2×YT medium containing 150 μg/ml of ampicillin at 37° C. for 10 hours with shaking (pre-incubation). The pre-incubation solution (0.5 ml) was added to 50 ml of 2×YT medium containing 150 μg/ml of ampicillin, and incubated at 37° C. for 20 hours with shaking.

Figure 3:
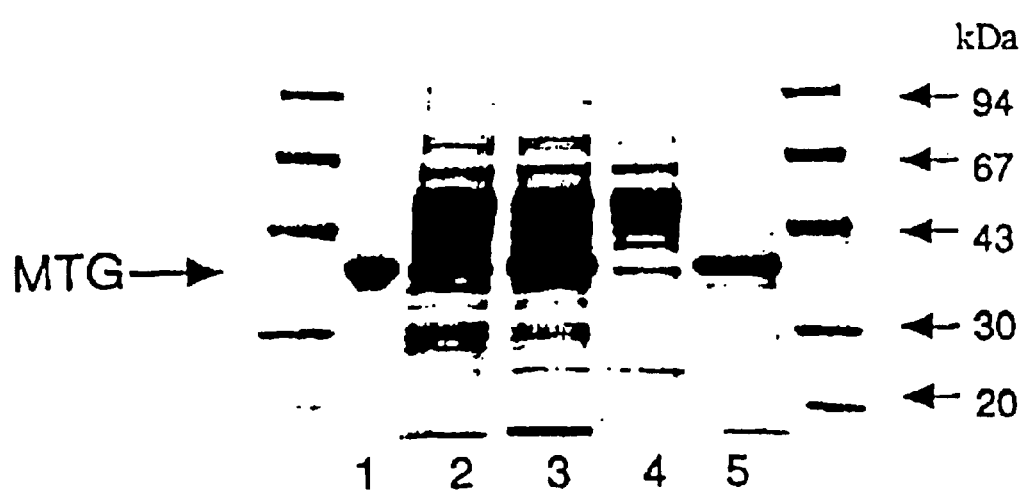
FIG. 3. SDS-polyacrylamide electrophoresis of MTG expression.

Cells were collected from the culture solution, and ultrasonically disrupted. All the fractions of the disrupted cell solution, the centrifugation supernatant fraction and the centrifugation precipitate fraction were analyzed by SDS polyacrylamide electrophoresis. The results are shown in FIG. 3. High expression of the protein having the same molecular weight as MTG was identified in the all fractions of the disrupted cell lysate and the centrifugation precipitate fraction in pUCTRPMTG-02 (+)/JM109. Further, it was identified by the Western blotting that this protein reacted with mouse anti-MTG antibody. The amount of this protein expressed was 500 to 600 mg/liter. Satisfactorily high expression was observed in the production medium without adding 3-β-indole acrylic acid thereto.

Moreover, the Western blotting was conducted using mouse anti-MTG antibody. Then, MTG was expressed only slightly in the centrifugation supernatant fraction, and it was found that almost all of MTG expressed was formed into an insoluble protein inclusion bodies.

<5> Analysis of the N-terminus Amino Acid of Expressed MTG

The protein inclusion bodies of expressed MTG was subjected to analysis of amino acid residues in the N-terminus. Consequently, approximately 60% was a methionine residue and approximately 40% a formylmethionine residue in the sequence of the N-terminus. For removing the formylmethionine residue corresponding to an initiation codon, the following procedure was conducted.

<6> Deletion of an Aspartic Acid Residue in the N-terminus of MTG

A base sequence corresponding to an aspartic acid residue was deleted by conducting PCR using pUCN216 containing 216 bases corresponding to the N-terminus of MTG as a template. pUCN216 is a plasmid obtained by cloning approximately 216 bp containing a ClaI-HpaI fragment of the N-terminus of MTG in EcoRI/HindIII site of pUC19. pF01 (SEQ ID No: 55) and pR01 (SEQ ID No: 56) are primers having sequences in the vector. pDELD (SEQ ID No: 57) is a primer in which a base sequence corresponding to an Asp residue is deleted, and pHd01 (SEQ ID No: 58) is a primer in which C is changed to G and HindIII site is crushed. pF01 and pDELD are sense primers, and pR01 and pHd01 are anti-sense primers.

First, pUCN216 was subjected to PCR using a combination of pF01 and pHd01 and a combination of pDELD and pR01 at 35 cycles under conditions of 94° C. and 30 seconds, 55° C. and 1 minute and 72° C. and 2 minutes, respectively. Each PCR product was extracted with a phenol/chloroform mixture, precipitated with ethanol, and dissolved in 100 μl of H₂O.

The respective PCR products were collected in amounts of 1 μl each, mixed, and thermally denatured at 94° C. for 10 minutes. Then, PCR was conducted at 35 cycles under conditions of 94° C. and 30 seconds, 55° C. and 1 minute and 72° C. and 2 minutes using a combination of primers pF01 and pHd01.

The second PCR product was extracted with a phenol/chloroform mixture, and precipitated with ethanol. The precipitate obtained was treated with HindIII and EcoRI and subjected to pUC19 subcloning to obtain pUCN216D (FIG. 4). The sequence of pUCN216D obtained was identified (confirmed) to be a desired one.

<7> Construction of a Plasmid with an Aspartic Acid Residue Deleted

An Eco0109I/HpaI fragment (small) of pUCN216D was ligated with an Eco0109I/HpaI fragment (large) of pUCB1-2 (plasmid in which an HpaI/HglII fragment of MTG gene was cloned in EcoRI/HindIII site of pUC 19) to form pUCNB1-2D. Further, a ClaI/BglII fragment (small) of pUCNB1-2D was ligated with a ClaI/BglII fragment (large) of pUCTRPMTG-02 (+), an MTG high expression plasmid to form MTG expression plasmid pUCTRPMTG(+)D2 with an aspartic acid residue removed (FIG. 5). As a result, a plasmid containing MTG gene with GAT corresponding to the aspartic acid residue deleted was obtained as shown in FIG. 6.

<8> Expression of MTG with an Aspartic Acid Residue Deleted

*E. coli* JM109 transformed with pUCTRPMTG(+)D2 was incubated in 3 ml of 2×YT medium containing 150 μg/ml of ampicillin at 37° C. for 10 hours with shaking (pre-incubation). The pre-incubation solution (0.5 ml) was added to 50 ml of 2×YT medium containing 150 μg/ml of ampicillin, and incubated at 37° C. for 20 hours with shaking. Cells were ultrasonically disrupted. The resulting disruption supernatant and precipitate were subjected to Coomassie Brilliant Blue staining and Western blotting with mouse anti-MTG antibody after SDS-polyacrylamide gel electrophoresis. Consequently, after the ultrasonic disruption, MTG protein with the aspartic acid residue deleted was detected in the precipitate, namely, the insoluble fraction. This indicates that the MTG protein with the aspartic acid residue deleted was intracellularly accumulated as a protein inclusion bodies.

Further, the protein inclusion bodies were subjected to analysis of an N-terminus amino acid sequence.

Consequently, as shown in FIG. 7, approximately 90% was serine in the sequence of the N-terminus.

A comparison of the results on the amino acid in the N-terminus of expressed MTG obtained in <5> and <8> are as shown in Table 1. It was found that initiation methionine added to the N-terminus of expressed MTG was efficiently removed by deletion of the aspartic acid residue in the N-terminus of MTG.

TABLE 1

| Strain | Terminal Amino Acid | | | |
|---|---|---|---|---|
| | f-Met | Met | Asp | Ser |
| pUCTRPMTG-02 (+)/JM109 | 40% | 60% | N.D. | — |
| pUCTRPMTG (+) D2/JM109 | N.D. | 10% | — | 90% |

N.D.: not detected.

Example 1

A granule suspension (1 mM EDTA) was prepared using granules (centrifugation precipitate fraction described above) produced as in Production Example for the starting material. Urea was added thereto in a final concentration of 8 M, and 20 mM DTT was further added thereto. The mixture was then adjusted to pH 7.5 with a 20 mM phosphate buffer, and extracted at 37° C. for 2 hours with stirring to form a denatured, enzyme solution. The content of the denatured enzyme was measured by the reverse phase HPLC described above, and then frozen and stored at −80° C. in small divided portions until it was used in the subsequent experiment.

Concentrated hydrochloric acid was added dropwise to the denatured enzyme solution (enzyme concentration: approximately 50 mg/ml) to adjust the pH value to 4.0. This was diluted with a 20 mM sodium phosphate containing 8 M urea and 20 mM dithiothreitol (DTT) (pH 4.0) to adjust the concentration of the denatured enzyme to 40 mg/ml. 0.25 ml of this solution was poured into 50 ml of a dilution buffer (20 mM sodium acetate containing 2 mM DTT, pH 4.0) previously cooled to 5° C. for dilution, and immediately homogenized with stirring. At this time, the reaction conditions were that the concentration of the denatured enzyme was 0.2 mg/ml and the urea concentration was 0.04 M. The enzymatic activity (specific activity) of the reaction solution measured by the hydroxamate method described in the literature (Bioscience, Biotechnology, and Biochemistry, 61, 830–835, 1997) was 19.4 U/mg. The stirring was continued at 5° C. for 30 minutes, and 4 M sodium hydroxide was then added thereto dropwise to increase the pH value to 6.0. Centrifugation was conducted to obtain a supernatant. The specific activity of the resulting enzyme was raised to 1.5 times compared with that before increasing the pH value, and reached 29.0 U/mg. It was approximately consistent with that of microorganism-derived transglutaminase in a native state. The recovery rate of the protein from the denatured enzyme was 53.6%.

While maintaining the foregoing refolding reaction conditions, only the experiment scale was increased to 10 times. The dilution was conducted with 500 ml of a buffer, and the pH was raised to 6.0. Subsequently, centrifugation was conducted to obtain a supernatant. The specific activity of this enzyme was 33.7 U/mg, and the recovery rate of the protein from the denatured enzyme solution was 41.9%. This enzyme solution was subjected to a cation exchange chromatography. The properties of the resulting purified enzyme were measured using (1) reverse phase HPLC (refer to FIG. 8), (2) CD spectrum (refer to FIG. 9) and (3) differential scanning calorimeter (DSC), and compared with those of microorganism-derived transglutaminase in a native state. Consequently, no substantial difference was found therebetween.

Example 2

Concentrated hydrochloric acid was added dropwise to a denatured enzyme solution prepared as in Example 1 to adjust the pH value to 4.0. This was diluted with a 20 mM sodium phosphate containing 8 M urea and 20 mM DTT (pH 4.0) to adjust the concentration of the denatured enzyme to 0.2 mg/ml. Six milliliters of this denatured enzyme solution was loaded onto Sephadex G-25M column (1.6 φ×15 cm, Amersham-Pharmacia-Biotech) equilibrated with a 20 mm sodium acetate buffer containing 2 mM DTT (pH 4.0), and eluted with the same buffer. A protein fraction was recovered using UV absorbance at wavenumber of 280 nm as an index. Chromatography was conducted at room temperature. The recovered fraction was cooled to 5° C. for 30 minutes or more, and 4 M sodium hydroxide was added dropwise thereto to increase the pH value to 6.0. Centrifugation was conducted to obtain a supernatant. The specific activity of this enzyme was 23.4 U/mg, and the recovery rate of the protein from the denatured enzyme solution was 39.8%. Thus, the specific activity and the recovery rate were all lower than those of the enzyme obtained in Example 1.

Example 3

Concentrated hydrochloric acid was added dropwise to a denatured enzyme solution prepared as in Example 1 to adjust the pH value to 4.0. This was diluted with a 20 mM sodium phosphate containing 8 M urea and 20 mM DTT (pH 4.0) to adjust the concentration of the denatured enzyme to 0.2 mg/ml. One milliliter of this denatured enzyme solution was poured on a dialysis membrane (Spectra/Por membrane, No. 1; Spectrum Medical Industries, Inc.), and dialyzed overnight against 1,000 ml of a buffer (20 mM sodium acetate containing 2 mM DTT, pH 4.0) at 5° C. 4 M sodium hydroxide was added dropwise to the resulting dialyzed solution to increase the pH value to 6.0. Centrifugation was conducted to obtain a supernatant. The specific activity of this enzyme was 31.1 U/mg, and the recovery rate of the protein from the denatured enzyme solution was 42.6% which was lower than the recovery rate of the protein obtained in Example 1.

Example 4

Concentrated hydrochloric acid was added dropwise to a denatured enzyme solution prepared in the same manner as in Example 1 to adjust. the pH value to 6.0. This was diluted with a 20 mM sodium phosphate containing 8 M urea and 20 mM DTT (pH 6.0) to adjust the concentration of the denatured enzyme to 40 mg/ml. This solution (0.25 ml) was poured into 50 ml of a dilution buffer (20 mM sodium acetate containing 2 mM DTT, pH 6.0) previously cooled to 5° C. for dilution, and immediately homogenized with stirring. At this time, the reaction conditions were that the concentration of the denatured enzyme was 0.2 mg/ml and the urea concentration was 0.04 M. The stirring was continued at 5° C. for 30 minutes, and centrifugation was conducted to obtain a supernatant. No protein was detected at all in the supernatant, and the denatured enzyme subjected to the refolding was all aggregated.

Further, 4 M sodium hydroxide was added dropwise to a denatured enzyme solution prepared in the same manner as in Example 1 to adjust the pH value to 9.0. This was diluted with a 20 mM sodium phosphate containing 8 M urea and 20 mM DTT (pH 9.0) to adjust the concentration of the denatured enzyme to 40 mg/ml. This solution (0.25 ml) was poured into 50 ml of a dilution buffer (20 mM Trishydrochloride containing 2 mM DTT, pH 9.0) previously cooled to 5° C. for dilution, and immediately homogenized with stirring. At this time, the recovery rate of the protein was 18.9%. However, no enzymatic activity was detected at all. Subsequently, Concentrated hydrochloric acid was added dropwise to decrease the pH value to 6.0, and centrifugation was conducted to obtain a supernatant. No protein was detected at all in the supernatant, and the denatured enzyme subjected to the refolding was all aggregated.

The foregoing results reveal that Example 1 is effective and the pH value in the dilution procedure has to be kept in an acidic region.

Example 5

Concentrated hydrochloric acid was added dropwise to a denatured enzyme solution prepared in the same manner as in Example 1 to adjust the pH value to 4.0. This was diluted with a 20 mM sodium phosphate containing 8 M urea and 20 mM DTT (pH 4.0) to adjust the concentration of the denatured enzyme to 40 mg/ml. This solution (0.25 ml) was poured into 50 ml of a dilution buffer (20 mM sodium acetate containing 2 mM DTT, pH 4.0) previously cooled to 5° C. for dilution, and immediately homogenized with stirring. The stirring was continued at 5° C. for 30 minutes, and 0.25 ml of the denatured enzyme solution (40 mg/ml, pH 4.0) was poured thereinto again for dilution. This procedure was further repeated twice, and the dilution was thus conducted in total four times in the divided dilution procedure. Consequently, the final reaction conditions were that the concentration of the denatured enzyme was 0.78 mg/ml and the urea concentration was 0.16 M. The stirring was continued at 5° C. for 30 minutes, and 4 M sodium hydroxide was then added dropwise to increase the pH value to 6.0. Centrifugation was conducted to obtain a supernatant. The specific activity of the resulting enzyme was 32.8 U/mg, and the recovery rate of the protein from the denatured enzyme solution was 59.0%. When 1 ml of the denatured enzyme solution (pH 4.0, 40 mg/ml) was poured at a time for dilution without dividing the dilution procedure, the specific activity of the resulting supernatant was the same (32.8 U/mg), but the recovery rate of the protein was 56% which was 3% lower than when the dilution was divided in four 20 parts.

Example 6

Concentrated hydrochloric acid was added dropwise to a denatured enzyme solution prepared in the same manner as in Example 1 to adjust the pH value to 4.0. This was diluted with a 20 mM sodium phosphate containing 8 M urea and 20 mM DTT (pH 4.0) to adjust the concentration of the denatured enzyme to 40 mg/ml. This solution (0.25 ml) was poured into 50 ml of a dilution buffer (20 mM sodium acetate containing 2 mM DTT, pH 4.0) previously cooled to 5° C. for dilution, and immediately homogenized with stirring. The stirring was continued at 5° C. for 30 minutes, $CaCl_2$ was added at a concentration of 1 mm, and the mixture was further stirred at 5° C. for 30 minutes. At this time, the reaction conditions were that the concentration of the denatured enzyme was 0.2 mg/ml, the urea concentration was 0.04 M and the $CaCl_2$ concentration was 1 mM. Subsequently, 4 M sodium hydroxide was added dropwise to increase the pH value to 6.0. Centrifugation was conducted to obtain a supernatant. The specific activity of the resulting enzyme was 30.0 U/mg, and the recovery rate of the protein from the denatured enzyme solution was 60.1%. As a control, the refolding was conducted at the same time without the addition of $CaCl_2$. Consequently, the specific activity of the resulting enzyme was 31.7 U/mg which was approximately the same as the foregoing value, but the recovery rate of the protein from the denatured enzyme solution was 51.3% which was different from the foregoing value by approximately 9%. It could prove the effect provided by the addition of $CaCl_2$ before the pH value was increased to 6.0.

Meanwhile, when $CaCl_2$ was previously added to the dilution buffer at a concentration of 1 mM, the specific activity was 25.3 U/mg, and the recovery rate of the protein was 53.2%. These were both lower than the values provided when it was added immediately before increasing the pH value.

Example 7

Concentrated hydrochloric acid was added dropwise to a denatured enzyme solution prepared in the same manner as in Example 1 to adjust the pH value to 4.0. This was diluted with a 20 mM sodium phosphate containing 8 M urea and 20 mM DTT (pH 4.0) to adjust the concentration of the denatured enzyme to 40 mg/ml.

This solution (0.25 ml) was poured into 50 ml of a dilution buffer (20 mM sodium acetate containing 2 mM DTT, pH 4.0) previously cooled to 5° C. for dilution, and immediately homogenized with stirring. The stirring was continued at 5° C. for 30 minutes, $StCl_2$ was added at a concentration of 0.1 mM, and the mixture was further stirred at 5° C. for 30 minutes. At this time, the reaction conditions were that the concentration of the denatured enzyme was 0.2 mg/ml, the urea concentration was 0.04 M and the $StCl_2$ concentration was 0.1 mM. Subsequently, 4 M sodium hydroxide was added dropwise to increase the pH value to 6.0. Centrifugation was conducted to obtain a supernatant. The specific activity of the resulting enzyme was 27.3 U/mg, and the recovery rate of the protein from the denatured enzyme solution was 84.5% which was greatly improved as compared with the recovery rate (53.6%) of the protein obtained in Example 1.

Example 8

Concentrated hydrochloric acid was added dropwise to a denatured enzyme solution prepared in the same manner as in Example 1 to adjust the pH value to 4.0. This was diluted with a 20 mM sodium phosphate containing 8 M urea and 20 mM DTT (pH 4.0) to adjust the concentration of the denatured enzyme to 40 mg/ml. This solution (0.25 ml) was poured into 50 ml of a dilution buffer (20 mM sodium acetate containing 2 mM DTT, pH 4.0) previously cooled to 5° C. for dilution, and immediately homogenized with stirring. The stirring was continued at 5° C. for 30 minutes, and CHAPS (3-[(3-cholamidoisopropyl)dimethylammonio]-2-hydroxy-1-propanesulfonate) as a surfactant was added at a concentration of 10 mM, and the mixture was further stirred at 5° C. for 30 minutes. At this time, the reaction conditions were that the concentration of the denatured enzyme was 0.2 mg/ml, the urea concentration was 0.04 M and the CHAPS concentration was 10 mM. Subsequently, 4 M sodium hydroxide was added dropwise to increase the pH value to 6.0. Centrifugation was conducted to obtain a supernatant. The specific activity of the resulting enzyme was 29.3 U/mg, and the recovery rate of the protein from the denatured enzyme solution was 93.0%, which was greatly improved as compared with the recovery rate (53.6%) of the protein obtained in Example 1.

Example 9

Concentrated hydrochloric acid was added dropwise to a denatured enzyme solution prepared in the same manner as in Example 1 to adjust the pH to 4.0. This was diluted with a 20 mM sodium phosphate containing 8 M urea and 20 mM DTT (pH 4.0) to adjust the concentration of the denatured enzyme to 40 mg/ml. This solution (0.2 ml) was poured into 10 ml of a dilution buffer (20 mM sodium acetate containing 2 mM DTT, pH 4.0) previously cooled to 5° C. for dilution, and immediately homogenized with stirring. While the stirring was continued at 5° C., 1 ml of the solution was sampled each after 30 seconds, 5 minutes, 0.5 hour, 1.0 hour, 1.5 hours, 2.0 hours, 3.0 hours and 17 hours. Immediately, 4 M sodium hydroxide was added dropwise to each sampled 1 ml solution to shift the pH value to 6.0, and centrifugation was conducted to obtain a supernatant. The relation of the specific activity of the enzyme in the resulting supernatant, the recovery rate of the protein from the denatured enzyme solution and the supernatant and the time that lapsed until the sampling (Retention Time) is shown in Table 2. Consequently, immediately after the dilution, the specific activity after the pH shifting was low. However, as the time until the sampling became longer, the specific activity of the supernatant after the pH shifting was increased, and reached 30 U/mg after 1.5 hours or more. It was thus found that for the intermediate structure (state) formed by the dilution at pH 4.0 to reach the structural state suited for the refolding, the time of 1.5 hours or more was preferably required.

TABLE 2

| Retention Time | Specific Activity (U/mg) | Recovery Rate of Protein (%) |
| --- | --- | --- |
| 30 seconds | 13.6 | 54.0 |
| 5 minutes | 15.7 | 50.8 |
| 0.5 hour | 24.1 | 43.8 |
| 1.0 hour | 27.1 | 50.5 |
| 1.5 hours | 30.6 | 50.2 |
| 2.0 hours | 30.1 | 54.5 |
| 3.0 hours | 31.1 | 54.9 |
| 17 hours | 29.7 | 58.5 |

Example 10

Concentrated hydrochloric acid was added dropwise to a denatured enzyme solution prepared in the same manner as in Example 1 to adjust the pH value to 4.0. This was diluted with 20 mM sodium phosphate containing 8 M urea and 20 mM DTT (pH 4.0) to adjust the concentration of the denatured enzyme to 40 mg/ml. This solution (0.2 ml) was poured into 10 ml of each of dilution buffers (20 mM sodium acetate containing 2 mM DTT) having various pH values (3.5, 3.8, 4.0, 4.2, 4.5, 5.0 and 5.5) and each previously cooled to 5° C. for dilution, and immediately homogenized with stirring. The stirring was continued at 5° C. for 2 hours, and 4 M sodium hydroxide was then added dropwise to shift the pH value to 6.0. Centrifugation was conducted to obtain a supernatant. The relation of the specific activity of the enzyme in the resulting supernatant, the recovery rate of the protein from the denatured enzyme solution, and the supernatant and the pH value in dilution is shown in Table 3. Consequently, the highest specific activity and recovery rate of the protein were obtained at pH 4.0 and pH 4.2.

TABLE 3

| pH in dilution | Specific Activity (U/mg) | Recovery Rate of Protein (%) |
| --- | --- | --- |
| 3.5 | 18.0 | 34.0 |
| 3.8 | 26.1 | 51.2 |
| 4.0 | 30.8 | 60.3 |
| 4.2 | 31.1 | 59.5 |
| 4.5 | 27.8 | 51.3 |
| 5.0 | 22.1 | 41.1 |
| 5.5 | 20.6 | 27.2 |

Example 11

Concentrated hydrochloric acid was added dropwise to a denatured enzyme solution prepared in the same manner as in Example 1 to adjust the pH value to 4.0. This was diluted with a 20 mM sodium phosphate containing 8 M urea and 20 mM DTT (pH 4.0) to adjust the concentration of the denatured enzyme to 40 mg/ml. This solution (147 ml) was poured into 7,350 ml of a dilution buffer (20 mm sodium acetate containing 2 mM DTT, pH 4.1) previously cooled to 5° C. for dilution, and immediately homogenized with stirring. The stirring was continued at 5° C. for 2 hours, and 4 M sodium hydroxide was then added dropwise to shift the pH value to 6.0. A supernatant was obtained by decantation and centrifugation. The specific activity of the enzyme in the resulting supernatant was 30.7 U/mg, and the recovery rate of the protein from the denatured enzyme solution and the supernatant was 66.5%. The supernatant was concentrated to 750 ml by ultra filtration (Hydrosalt, 10 kDa molecular weight—cutoff; SARTOCON Slice Cassette, manufactured by Saltorius), and diluted 10-fold with an equilibration buffer (20 mM sodium acetate, pH 5.8) in the cation exchange chromatography. Subsequently, the solution was loaded onto a cation exchange column (CM Sepharose FF, 11.3 φ×10 cm; manufactured by Amersham-Pharmacia-Biotech) fully equilibrated with the same buffer. After re-equilibration with the same buffer, a protein fraction (500 ml) eluted with a 0→0.3 M NaCl linear concentration gradient using UV absorbance at wavelength of 280 nm as an index was recovered. Chromatography was conducted at room temperature. This procedure could remove cell-derived non-protein impurities. A half amount (250 ml) of the fraction recovered was loaded onto a gel filtration column (Sephadex G-25M, 14 φ×15 cm; manufactured by Amersham•Pharmacia•Biotech) equilibrated with a 20 mM sodium phosphate buffer containing 2 mM DTT (pH 6.0), and eluted with the same buffer. The protein fraction (380 ml) was recovered using UV absorbance at wavelength of 280 nm as an index. Chromatography was conducted at room temperature. The specific activity of the resulting protein fraction was 29.4 U/mg (approximately 0.75 g). This fraction was adjusted to a concentration of 1.2 mg/ml, and frozen and stored in small divided portions at −80° C. This stored sample is hereinafter referred to as "purified recombinant-type transglutaminase".

Meanwhile, the remaining half amount (250 ml) of the fraction recovered in the cation exchange chromatography described above was loaded onto the gel filtration column as described above equilibrated with a 10 mM ammonium acetate buffer containing 2 mM DTT (pH 6.0), and eluted with the same buffer. The protein fraction (380 ml) was recovered MM using UV absorbance at wavelength of 280 nm as an index. Chromatography was conducted at room temperature. The total amount of the resulting protein fraction was concentrated to 122 ml by using the ultra filtration as described above. This was adjusted such that the final concentration of ammonium acetate reached to 50 mM, frozen at −80° C., and then freeze-dried to obtain approximately 0.75 g of a powder. This powder is hereinafter referred to as a "purified recombinant-type transglutaminase powder".

Example 12

Using the purified recombinant-type transglutaminase powder obtained in Example 11, the physicochemical properties of the intermediate structure (state) in the structural construction were measured. This powder was dissolved in a 1 mM EDTA aqueous solution, and urea, DTT and sodium phosphate were added such that the final concentrations thereof were 8 M, 20 mM and 20 mM, respectively to adjust the pH value to 7.5. The mixture was incubated at 37° C. for 2 hours, and Concentrated hydrochloric acid was added dropwise thereto to adjust the pH value to 4.0. This was diluted with a 20 mM sodium phosphate containing 8 M urea and 20 mM DTT (pH 4.0) to adjust the concentration of the denatured enzyme to 40 mg/ml. The resulting solution was frozen and stored at −80° C. in small divided portions until it was used in the subsequent experiments. After this denatured enzyme solution was dissolved, 0.2 ml of this solution was poured into 10 ml of a dilution buffer (20 mM sodium acetate containing 2 mM DTT, pH4.0)for dilution, and immediately homogenized with stirring. Subsequently, the near ultraviolet spectrum thereof was measured over time. In the measurement, JascoJ-715 spectropolarimeter was used. A 1-cm-pass cuvette was used in the near ultraviolet region, and a 0.1-cm-pass cuvette in the far ultraviolet region respectively. The measurement was conducted at room temperature with a wavelength scanning rate of 10 nm/min. The data obtained was converted to a CD (circular dichroism) signal per 1 mol of an amino acid. The near ultraviolet CD (circular dichroism) spectrum is shown in FIG. 10. The data of one scanning is shown in 0 to 10 min., the average data of five scannings in 10 to 60 min., and the average data of ten scannings each in 60 to 160 min. and 170 to 270 min., respectively. From the results, it was found that almost no higher-order structure was formed immediately after the dilution and thereafter the formation of the structure slowly proceeded. In 60 to 160 min. and 170 to 270 min., approximately the same spectrum was shown, which revealed that the formation of the higher-order structure observed in the near ultraviolet—CD was completed by 160 min. at the latest. Even after 26 hours from the dilution, the structure formed in 60 to 160 min. remained unchanged.

At the same time, urea, and sodium acetate were also added to the purified recombinant-type transglutaminase obtained in Example 11, and it was finally adjusted to pH 4.2 with a 20 mM sodium acetate containing 0.16 M urea and 2 mM DTT. The solution was allowed to stand for 24 hours, and a satisfactorily stable structure was formed in the same buffer.

Then, the CD spectrum was likewise measured, and compared with that in the native state. The results are shown in FIG. 11. The enzyme did not lose the native structure (state) even in 0.16 M urea at pH 4.2. Meanwhile, the structural state formed from the denatured state by the dilution (26 hours after the dilution) was clearly different from the structural state (native state) of this enzyme in the same buffer. It was found that the structural state formed by denaturation→dilution procedure (refolding) was the "intermediate state" different from the native state, and further the state was gradually changed after the dilution.

In view of the foregoing, it was found that the molecular ellipticity of the intermediate state was 30 to 70% of that of the native state in the CD spectrum of the near ultraviolet region, especially 260 to 290 nm.

Example 13

Concentrated hydrochloric acid was added dropwise to a denatured enzyme solution prepared in the same manner as in Example 12 to adjust the pH value to 4.0. This was diluted with a 20 mM sodium phosphate containing 8 M urea and 20 mM DTT (pH 4.0) to adjust the concentration of the denatured enzyme to 40 mg/ml. This solution (0.2 ml) was poured into 10 ml of a dilution buffer (20 mM sodium acetate containing 2 mM DTT, pH 4.0) for dilution, and immediately homogenized with stirring. In order to examine the change in the structural state after the dilution, gel filtration analysis was conducted using Superdex 75 HR 10/30. A 0.1 M sodium phosphate containing 0.02% Tween 20 (pH 4.0) was used for buffer, and a flow rate was 0.8 ml/min. One hundred micrograms (100 μg) of the sample after the dilution was analyzed over the course of time (2, 10, 30, 60, 100, 160 and 260 minutes, and 1 day). Immediately after the dilution (2 minutes), the peak was detected earlier by approximately 4 minutes than when the peak of the enzyme in the native structure IS (state) appeared. However, the elution time was changed over the course of time after the dilution. It was found that the structural state (size or form of a molecule) was continuously changed after the dilution.

Meanwhile, the purified gene recombinant-type transglutaminase obtained in Example 11 was dialyzed against a 20 mM sodium acetate containing 0.16 M urea and 2 mM DTT (pH 4.0) for 24 hours, a satisfactorily stable structure was formed in the dilution buffer, and the analysis was then likewise conducted (refer to FIG. 12). The elution time of the peak remained unchanged from the native state. Thus, the enzyme did not lose the native state even in 0.16 M urea at pH 4.0. When much time lapsed, the structure formed by the dilution agreed with the native structure with respect to the peak elution time. However, both the structures were still sharply different in the peak form. From the results, it was found that the intermediate state formed by the dilution was changed in its structure over the course of time, finally did not come to have the same structure as the native state and remained the intermediate state in the structural construction.

Example 14

Concentrated hydrochloric acid was added dropwise to a denatured enzyme solution prepared in the same manner as in Example 12 to adjust the pH value to 4.0. This was diluted with a 20 mM sodium phosphate containing 8 M urea and 20 mM DTT (pH 4.0) to adjust the concentration of the denatured enzyme to 15 mg/ml. This solution (0.2 ml) was poured into 10 ml of a dilution buffer (20 mM sodium acetate containing 2 mM DTT, pH 4.0), and immediately homogenized with stirring. This solution was excited at 280 nm, and $\lambda_{max}$ of Trp fluorescence was measured over the course of time (30 seconds, 0.5 hour, 1 hour, 1.5 hours and 2 hours). From immediately after the dilution (30 seconds), blue shifting (351.5→344 nm) of $\lambda_{max}$ was observed over the course of time, and it was shown that the structure gradually became compact (structural construction proceeded). Further, even after much time lapsed from the dilution, $\lambda_{max}$ did not agree with that (340.0 nm) in the native state, which revealed that the structural state formed by the dilution was no doubt different from the native state.

Meanwhile, the purified gene recombinant-type transglutaminase obtained in Example 11 was dialyzed against (with) a 20 mM sodium acetate containing 0.16 M urea and 2 mM DTT (pH 4.0) for 24 hours, and a satisfactorily stable structure was formed in the dilution buffer. Then, $\lambda_{max}$ of Trp fluorescence was likewise measured. Consequently, $\lambda_{max}$ was not different from that in the native state, and it was found that the enzyme maintained the native structure (state) even in 0.16 M urea at pH 4.0 (refer to Table 4). These results revealed; that the intermediate state formed by the dilution was changed in its structure over the course of time, that it did not come to have the same final structure as the native state; and that it remained in the intermediate state in the structural construction.

TABLE 4

| Retention Time | $\lambda_{max}$ (nm) |
| --- | --- |
| 30 seconds | 351.5 |
| 0.5 hour | 346.5 |
| 1 hour | 346.0 |
| 1.5 hours | 345.0 |
| 2 hours | 341.5 |
| Native Type (after dialysis) | 340.0 |

Example 15

Concentrated hydrochloric acid was added dropwise to a denatured enzyme solution prepared in the same manner as in Example 12 to adjust the pH value to 4.0. This was diluted with a 20 mM sodium phosphate containing 8 M urea and 20 mM DTT (pH 4.0) to adjust the concentration of the denatured enzyme to 15 mg/ml. This solution (0.2 ml) and ANS (8-anilinonaphthalene-1-sulfonic acid, final concentration 20 µM) were poured into 10 ml of a dilution buffer (20 mM sodium acetate containing 2 mM DTT, pH 4.2), and immediately homogenized with stirring. Subsequently, the ANS fluorescence intensity was measured at excitation wavelength of 400 nm and fluorescence wavelength of 470 nm over the course of time (1 minute, 0.5 hour, 1 hour, 1.5 hours and 2 hours). The results are shown in Table 5. As a result, the decrease in fluorescence intensity (1,387→974) with time was observed from immediately after the dilution (1 minute) to 2 hours, and it was shown that the hydrophobic region exposed on the protein surface gradually disappeared in the process. However, although much time lapsed after the dilution, the ANS fluorescence intensity did not decrease to the fluorescence intensity of the native state, showing that the structural state formed by the dilution was no doubt different from the native state.

Meanwhile, the purified gene recombinant-type transglutaminase obtained in Example 11 was dialyzed against (with) a 20 mM sodium acetate containing 0.16 M urea and 2 mM DTT (pH 4.2) for 24 hours, and a satisfactorily stable structure was formed in the dilution buffer. Then, the ANS fluorescence intensity was likewise measured. Consequently, the fluorescence intensity was somewhat increased as compared with that in the native state, but the change was very slight (56→162). Thus, the enzyme was found to maintain the native state even in 0.16 M urea at pH 4.2. These results revealed; that the intermediate state formed by the dilution was changed in its structure over the course of time, that it did not come to have the same final structure as that of the native state, and that it remained in the intermediate state in the structural construction.

TABLE 5

| Retention Time | ANS Fluorescence Intensity |
| --- | --- |
| 1 minute | 1.387 |
| 0.5 hour | 1,119 |
| 1 hour | 1,013 |
| 1.5 hours | 955 |
| 2 hours | 974 |
| Native Type (after dialysis) | 162 |

Example 16

Concentrated hydrochloric acid was added dropwise to a denatured enzyme solution prepared in the same manner as in Example 12 to adjust the pH value to 4.0. This was diluted with a 20 mM sodium phosphate containing 8 M urea and 20 mM DTT (pH 4.0) to adjust the concentration of the denatured enzyme to 40 mg/ml. This solution (0.2 ml) was poured into 10 ml of a dilution buffer (20 mm sodium acetate containing 2 mM DTT, pH 4.0), immediately homogenized with stirring, and subjected to a native-PAGE. The electrophoresis was conducted using a His-Mes buffer system (pH 6.1) with commercial NuPAGE Tris-Acetate 7% gel (Novex). The results are shown in FIG. 13. After dilution the enzyme exhibited mobility clearly different from that in the native state, showing that the structural state formed by the dilution was different from the native state.

Further, at the same time, an urea and a sodium acetate aqueous solution was added to the purified recombinant-type transglutaminase obtained in Example 11. The solution was finally adjusted to pH 4.0 with a 20 mM sodium acetate containing 0.16 M urea and 2 mM DTT, and likewise subjected to a native-PAGE. Consequently, the mobility was unchanged before and after the change in the composition of the solvent. Thus, it was found that the enzyme maintained the native state even in 0.16 M urea at pH 4.2.

The results shown in Examples 11 to 16 reveal that (1) the structural state formed by the dilution with the denaturant in the aqueous medium under the acidic condition is a complicated mixture, (2) this state is changed over the course of time and (3) it remains finally the "intermediate state" different from the native structure. Moreover, Examples 9 and 10 indicate that (4) the recovery rate to the native state can be improved by properly determining the dilution conditions to induce the desirable intermediate state.

Obviously, numerous modifications and variations on the present invention are possible in light of the above teachings. It is therefore to be understood that within the scope of the appended claims, the invention may be practiced otherwise than as specifically described herein.

What is claimed is:

1. A process for producing transglutaminase having an enzymatic activity comprising:

(a) incubating a denatured transglutaminase in an acidic aqueous medium;

(b) diluting the denatured transglutaminase in the acidic aqueous medium by about 5-fold to about 400-fold; and (c) adjusting the pH of said aqueous medium to a neutral pH by adding an alkali to said aqueous medium, wherein said acidic aqueous medium in step (a) has a pH of from 3 to 5.

2. The process as claimed in claim 1, wherein the aqueous medium further comprises a reducing agent.

3. The process as claimed in claim 2, wherein the reducing agent is selected from the group consisting of dithiothreitol, 2-mercaptoethanol, and tris-(2-carboxyethyl)phosphine.

4. The process as claimed in claim 1, wherein the denatured transglutaminase is obtained by a process comprising denaturing transglutaminase, which is expressed in a recombinant host cell, in the presence of a protein denaturant.

5. The process as claimed in claim 4, wherein the protein denaturant is selected from the group consisting of urea, guanidine hydrochloride, and thiocyanate.

6. The process as claimed in claim 4, wherein the transglutaminase concentration is from 10 to 100 mg/ml and the protein denaturant concentration is from 4 to 10 M.

7. The process as claimed in claim 1, wherein the aqueous medium in step (a) further comprises a protein denaturant.

8. The process as claimed in claim 7, wherein the protein denaturant is selected from the group consisting of urea, guanidine hydrochloride, and thiocyanate.

9. The process as claimed in claim 7, wherein the transglutaminase concentration is at least 40 mg/ml and the protein denaturant concentration is from 4 to 10 M.

10. The process as claimed in claim 1, wherein said acidic aqueous medium in step (a) has a pH of from 3.5 to 4.5.

11. The process as claimed in claim 1, wherein said denatured transglutaminase is diluted at least 5-fold.

12. The process as claimed in claim 1, wherein said denatured transglutaminase is diluted at least 10-fold.

13. The process as claimed in claim 1, wherein said denatured transglutaminase is diluted at least 50-fold.

14. The process as claimed in claim 1, wherein said incubation is performed at a temperature of not more than 15° C.

15. The process as claimed in claim 1, wherein said incubation is performed at a temperature of from 3 to 10° C.

16. The process as claimed in claim 1, wherein after said diluting in step (b) said denatured transglutaminase is at a concentration of not more than 10 mg/ml.

17. The process as claimed in claim 1, wherein said neutral pH is from 5.8 to 8.5.

18. The process as claimed in claim 1, wherein said neutral pH is from 6 to 7.

19. The process as claimed in claim 1, wherein in step (c), the aqueous medium further comprises an accelerator for forming a higher-order native-state transglutaminase structure having enzymatic activity.

20. The process as claimed in claim 19, wherein the accelerator is selected from the group consisting of an inorganic salt, an organic salt, an amino acid salt, a polyol, an organic solvent, and a surfactant.

21. The process as claimed in claim 20, wherein the accelerator is an inorganic salt accelerator, which is selected from the group consisting of calcium chloride and strontium chloride.

22. The process as claimed in claim 21, wherein the inorganic salt accelerator concentration is from 0.01 to 10 mM.

23. The process as claimed in claim 20, wherein the accelerator is an organic salt accelerator, which is selected from the group consisting of sodium acetate and sodium propionate.

24. The process as claimed in claim 23, wherein the organic salt accelerator concentration is from 0.1 to 2 M.

25. The process as claimed in claim 20, wherein the accelerator is an amino acid salt accelerator and is arginine hydrochloride.

26. The process as claimed in claim 25, wherein the amino acid salt accelerator concentration is from 0.1 to 2 M.

27. The process as claimed in claim 20, wherein the accelerator is a polyol accelerator and is polyethylene glycol.

28. The process as claimed in claim 27, wherein the polyol accelerator concentration is from 1 to 10%.

29. The process as claimed in claim 20, wherein the accelerator is an organic solvent accelerator which is selected from the group consisting of DMSO and DMF.

30. The process as claimed in claim 29, wherein the organic solvent accelerator concentration is from 10 to 40%.

31. The process as claimed in claim 20, wherein the accelerator is a surfactant and is CHAPS.

32. The process as claimed in claim 31, wherein the surfactant concentration is from 1 to 50 mM.

33. The process as claimed in claim 1, further comprising:

(d) centrifugating the aqueous medium of (c).

34. An isolated transglutaminase obtained by the process of claim 1, which has a structure having a molecular ellipticity which is 30 to 70% of that of a native-state tranaglutaminase in a CD spectrum of a near ultraviolet region.

35. The process as claimed in claim 1, wherein step (c) further comprises incubating the aqueous medium for more than 1.5 hours subsequent to adjusting the pH to a neutral region.

36. A food comprising the transglutaminase of claim 34.

37. The food of claim 36, which is a jelly, yogurt, cheese or meat.

38. A toiletry comprising the transglutaminase of claim 34.

39. In a method of producing a food comprising a transglutaminase, the improvement comprising producing the transglutaminase according to the process of claim 1.

* * * * *